(12) United States Patent
Shavit et al.

(10) Patent No.: US 12,285,362 B2
(45) Date of Patent: Apr. 29, 2025

(54) SYSTEM AND METHOD FOR TREATING BLEPHARITIS USING TISSUE STRESSING

(71) Applicant: NOVOXEL LTD., Netanya (IL)

(72) Inventors: Ronen Shavit, Tel Aviv (IL); Raphi Shavit, Tel Aviv (IL)

(73) Assignee: NOVOXEL LTD, Netanya (IL)

( * ) Notice: Subject to any disclaimer, the term of this patent is extended or adjusted under 35 U.S.C. 154(b) by 422 days.

(21) Appl. No.: 17/616,609

(22) PCT Filed: Jun. 5, 2020

(86) PCT No.: PCT/IL2020/050632
§ 371 (c)(1),
(2) Date: Dec. 3, 2021

(87) PCT Pub. No.: WO2020/245833
PCT Pub. Date: Dec. 10, 2020

(65) Prior Publication Data
US 2022/0226152 A1 Jul. 21, 2022

Related U.S. Application Data

(60) Provisional application No. 63/034,620, filed on Jun. 4, 2020.

(30) Foreign Application Priority Data

Jun. 6, 2019 (IL) .......................................... 267166

(51) Int. Cl.
*A61F 9/007* (2006.01)
*A61B 18/00* (2006.01)
(Continued)

(52) U.S. Cl.
CPC ........ *A61F 9/00772* (2013.01); *A61B 18/082* (2013.01); *A61B 18/10* (2013.01);
(Continued)

(58) Field of Classification Search
CPC ....... A61B 18/082; A61B 18/08; A61B 18/14; A61B 2018/0095; A61B 2018/0013;
(Continued)

(56) References Cited

U.S. PATENT DOCUMENTS 6,254,590 B1 * 7/2001 Vaillancourt ........... A61F 9/013
604/297
8,083,787 B2 12/2011 Korb et al.
(Continued)

FOREIGN PATENT DOCUMENTS

CN 109561984 A 4/2019
JP 2010504769 A 2/2010
(Continued)

OTHER PUBLICATIONS

Extended European Search Report received for EP Serial No. 20819466.2, received on Jul. 10, 2023.
(Continued)

*Primary Examiner* — Ronald Hupczey, Jr.
(74) *Attorney, Agent, or Firm* — Merchant & Gould P.C.

(57) ABSTRACT

A dermal conditioning device is for creating at least one pressure point on at least an external surface of an eyelid. The device includes at least one skin tissue lesion generator, at least one controller, a power supply and a housing, the controller coupled to the skin tissue lesion generator. A power supply couples to the skin tissue lesion generator and the controller and the housing encasing the skin tissue lesion generator and the controller. The controller controls the skin tissue lesion generator to generate at least one signal and to apply the signal to stress the external surface of an outer layer of the eyelid, the stress causing a formation of the pressure point on the eyelid without tissue coagulation, thereby activating at least one of a corneal reflex, a menace (Continued)

reflex, and a lacrimation reflex of the eyelid by activating at least one nociceptor on the eyelid.

24 Claims, 19 Drawing Sheets

(51) Int. Cl.
| | |
|---|---|
| *A61B 18/08* | (2006.01) |
| *A61B 18/10* | (2006.01) |
| *A61B 18/12* | (2006.01) |
| *A61B 18/14* | (2006.01) |
| *A61F 7/00* | (2006.01) |

(52) U.S. Cl.
CPC .......... *A61B 18/1206* (2013.01); *A61B 18/14* (2013.01); *A61B 2018/00452* (2013.01); *A61B 2018/00589* (2013.01); *A61B 2018/00702* (2013.01); *A61B 2018/00714* (2013.01); *A61B 2018/00761* (2013.01); *A61B 2018/087* (2013.01); *A61F 2007/0004* (2013.01)

(58) Field of Classification Search
CPC ........... A61B 2018/00142; A61B 2018/00148; A61B 2018/0019; A61B 2018/00196; A61B 2018/00452; A61B 2018/00625; A61B 2018/00916; A61B 2018/00994; A61B 2018/143; A61B 2018/00107
See application file for complete search history.

(56) References Cited

U.S. PATENT DOCUMENTS

| | | | |
|---|---|---|---|
| 9,510,972 B2 | 12/2016 | Badawi | |
| 9,719,977 B2 | 8/2017 | Korb et al. | |
| 2003/0212396 A1 | 11/2003 | Eggers et al. | |
| 2007/0060988 A1 | 3/2007 | Grenon et al. | |
| 2011/0046614 A1 | 2/2011 | Boxer Wachler | |
| 2013/0053733 A1 | 2/2013 | Korb et al. | |
| 2014/0221908 A1 | 8/2014 | Sonsino et al. | |
| 2015/0148711 A1 | 5/2015 | Bujak et al. | |
| 2016/0317208 A1* | 11/2016 | Slatkine | A61B 18/08 |
| 2016/0367806 A1 | 12/2016 | Kahook | |
| 2018/0104514 A1* | 4/2018 | Gertner | A61N 7/00 |

FOREIGN PATENT DOCUMENTS

| | | |
|---|---|---|
| WO | 2016070134 A1 | 5/2016 |
| WO | 2018024753 A1 | 2/2018 |
| WO | 2018/039729 A1 | 3/2018 |

OTHER PUBLICATIONS

International Search Report and Written Opinion for PCT/IL2020/050632 (Nov. 6, 2020).
Fossataro et al., "Hand blink reflex in virtual reality: the role of vision and proprioception in modulating defensive responses" (First published 2019).
Knop et al., "International Workshop on Meibomian Gland Dysfunction: Report of the Subcommittee on Anatomy, Physiology, and Pathophysiology of the Meibomian Gland", Investigative Ophthalmology & Visual Science, Special Issue, vol. 52, No. 4:1938-1978 (2011).
C. Belmonte, M. C. Acosta, J.M. Lloves, J. Gallar, "What Causes Eye Pain?", Curr. Ophthalmol. Rep. (2015) 3:111-121 doi: 10.1007/s40135-015-0073-9.
Zhi-Qiang Xue et al, "Implications of the epidermal growth factor on burn skin wound repair. An in vitro and in vivo study", Int J Clin Exp Med 2017;10(2):2648-2653, www.ijcem.com /ISSN:1940-5901/IJCEM0035104.
Laato, M., et al. "Stimulation of wound healing by epidermal growth factor. A dose-dependent effect." Annals of surgery 203.4: 379-381 (1986).
De Masi et al. "The influence of growth factors on skin wound healing in rats." Brazilian journal of otorhinolaryngology 82.5: 512-521 (2016).
Y. J. Zhu et al, "A multi-scale view of skin thermal pain: from nociception to pain sensation", Phil. Trans. R. Soc. A 368, 521-559 (2010).
G.D. Iannetti et al, "Aδ nociceptor response to laser stimuli: selective effect of stimulus duration on skin temperature, brain potentials and pain perception", Clinical Neurophysiology 115: 2629-2637 (2004).
Adrienne E. Dubin et al, "Nociceptors: the sensors of the pain pathway", The Journal of Clinical Investigation http://www.jci.org vol. 120 No. 11 Nov. 2010.
Rodrigo Bolaños-Jiménez et al, "Ocular Surface as Barrier of Innate Immunity", The Open Ophthalmology Journal, 9:49-55 (2015).
Eearl O. Butcher Ph.D., et al, "The Physical Properties Of Human Sebum", the journal of investigative dermatology: 249-254 (1949).
P S Tsai, J E Evans et al, "Proteomic analysis of human meibomian gland secretions", Br J Ophthalmol, 90:372-377 (2006).
Fei Dong et al, "Role of EGF Receptor Signaling on Morphogenesis of Eyelid and Meibomian Glands", Published in final edited form as: Exp Eye Res., 163: 58-63 (2017).
Kazuo Tsubota, "Tear Dynamics and Dry Eye", Progress in Retinal and Eye Research vol. 17, No. 4: 565-596 (1998).
Steven P. Arnoczky et al, "Thermal Modification of Connective Tissues: Basic Science Considerations and Clinical Implications", Journal of the American Academy of Orthopaedic Surgeons, vol. 8, No. 5 (2000).
Neil Sadick, MD, "Tissue Tightening Technologies: Fact or Fiction", Aesthetic Surgery Journal, vol. 28: 180-188 (2008).
Peterson DC, Hamel RN. "Corneal Reflex" [Updated Jun. 22, 2019]. In: StatPearls [Internet]. Treasure Island (FL): StatPearls Publishing (2019).
CN Search Report issued for Chinese Patent Application No. 2020800492870 dated Jul. 1, 2024, with English translation.
JP Office Action issued for Japanese Patent Application No. 2021-571863 mailed Dec. 26, 2023, with English translation.

* cited by examiner

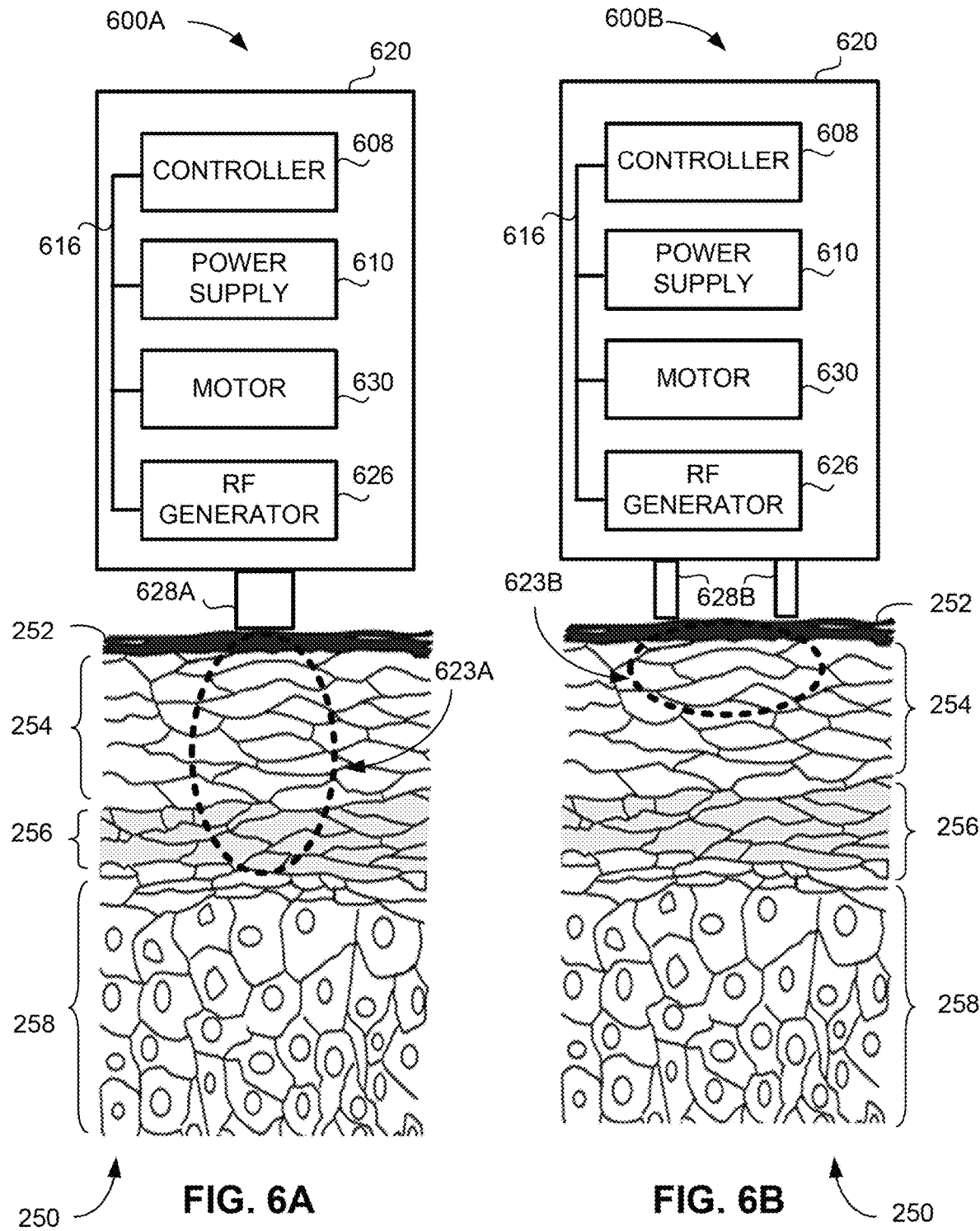

SYSTEM AND METHOD FOR TREATING BLEPHARITIS USING TISSUE STRESSING

This application is a National Stage application of PCT/IL2020/050632, filed Jun. 5, 2020, which claims priority to U.S. Provisional Patent Application No. 63/034,620, filed Jun. 4, 2020, and Israeli Patent Application No. 267166 filed Jun. 6, 2019, which applications are incorporated herein by reference. To the extent appropriate, a claim of priority is made to each of the above-disclosed applications.

FIELD OF THE DISCLOSED TECHNIQUE

The disclosed technique relates to systems and methods for blepharitis treatment, in general, and to systems and methods for inducing eye reflexes via the eyelids while preventing permanent damage to the skin tissue of the eyelids, in particular.

BACKGROUND OF THE DISCLOSED TECHNIQUE

Skin is a dynamic, multi-layered organ in a constant state of change as cells of the uppermost, outer layers are shed and replaced by inner cells moving up to the surface of the skin. Although structurally consistent throughout the body, skin varies in thickness according to anatomical site and age of the individual. Anatomically speaking, the epidermis is the outermost layer, serving as the physical and chemical barrier between the interior body and exterior environment; the dermis is a deeper layer providing structural support for the skin, while the subcutis or hypodermis is a layer deeper than the dermis which acts as an important depot of fat. The dermis is a layer made up of loose connective tissue.

The mammalian eye is a complex organ enabling vision in mammals, including the conscious perception of light, color differentiation and the perception of depth. The eye is broadly made up of three layers which enclose various anatomical structures. The outermost layer, known as the fibrous tunic, is composed of the sclera and the cornea. The sclera is known as the white of the eye in the vernacular, and covers most of the outer surface of the eye. The cornea is the transparent part of the eye which allows light to enter the eyeball and reach the optic nerve. Under the fibrous tunic is the uvea, a middle layer which includes the iris and under the uvea is the retina, the inner most layer of the eye which connects with the optic nerve.

The cornea and the sclera are exposed to the environment and surrounding conditions and with the help of the eyelids and eyelashes, keep irritants and debris out of the eye. Similar to skin in general, the cornea and sclera are lubricated with a bodily substance called lacrimal fluid, commonly known as tears, which often serve to clean and lubricate the eyes in response to irritation. Lacrimal fluid is produced by the lacrimal gland which sits on the upper lateral region of the eye socket in the skull of a mammal. When the eyes blink, the lacrimal fluid is spread across the exposed sclera and cornea (i.e., the surface of the eye) which collects in the medial corner of the eye in an area known as the lacrimal lake. From there, the lacrimal fluid is drained into the lacrimal sac. The lacrimal fluid which spreads across the surface of the eye is referred to medically as the tear film or the precorneal film and constantly coats and lubricates the sclera and the cornea. The tear film itself has three distinct layers, an outermost lipid layer containing mainly oils, a middle aqueous layer containing electrolytes, amino acids and proteins and an inner mucous layer containing mainly mucins. The lipid layer of the tear film, known as meibum or sebum, is produced by the Meibomian gland (one for each eye) which sits at the rim of the eyelids inside the tarsal plate. The lipid layer coats the aqueous layer, preventing the aqueous layer from evaporating and from spilling over onto the cheeks. The aqueous layer of the tear film is produced by the lacrimal gland (one for each eye) and forms the bulk of the tear film while also promoting the spreading of the tear film over the surface of the eye. The mucous layer is produced by conjunctival goblet cells, directly coating the cornea and enabling an even distribution of the tear film over the surface of the eye.

Reference is now made to FIG. 1A, which shows schematic illustrations of the eye showing the organs involved in tear film production, generally referenced 10 and 40, as is known in the prior art. Upper illustration 10 shows a cross-section of the eye whereas lower illustration 40 shows a frontal view of the eye. With reference to upper illustration 10, shown is an eyeball 12 having a pupil 14 and a cornea 16. Above the surface of cornea 16 is a tear film 18 which includes three layers. As shown by a box 20, the three layers of tear film 18 are shown in an expanded view to include a lipid layer 22, an aqueous layer 24 and a mucous layer 26. Lipid layer 22 is the outermost layer whereas mucous layer 26 rest directly on cornea 16. The top and bottom part of eyeball 12 is covered by eyelids 27A and 27B which have a plurality of eyelashes 28 which extend therefrom. The upper eyelid 27A includes a lacrimal gland 30 as well as a Meibomian gland 32A whereas lower eyelid 27B only includes Meibomian gland 32B. Whereas not shown explicitly, eyelids 27A and 27B include an orbicularis muscle, forming the bulk of eyelids 27A and 27B, positioned between the skin (not referenced) of eyelids 27A and 27B and the glands shown in FIG. 1A. The orbicularis muscle substantially surrounds the eye and is the muscle responsible for opening and closing eyelids 27A and 27B. Thus the orbicularis muscle enables the eye to blink and is contracted and relaxed when an eye reflex that causes blinking is activated. A conjunctiva 34 lines the insides of eyelids 27A and 27B and as shown, lacrimal gland 30 as well as Meibomian glands 32A and 32B are coupled with conjunctiva 34. A plurality of goblet cells 36 lies on conjunctiva 34. Each of lacrimal gland 30, Meibomian glands 32A and 32B and plurality of goblet cells 36 together produce the components which make up tear film 18. Meibomian glands 32A and 32B produce lipid layer 22, lacrimal gland 30 produces aqueous layer 24 and plurality of goblet cells 36 produces mucous layer 26. As shown in greater detail in lower illustration 40, each time eyelids 27A and 27B open and close via the orbicularis muscle in the action known as blinking, tear film 18 is excreted from the combination of liquids produced by lacrimal gland 30, Meibomian glands 32A and 32B and plurality of goblet cells 36 and travels across the cornea, thereby keeping the surface of the cornea fluid and clean.

Reference is now made to lower illustration 40, showing a frontal view of an eye. Shown is an eyelid 42, a cornea 44 and an iris 46. Hidden under the skin but shown in lower illustration 40 is a lacrimal gland 48, a Meibomian gland 50 as well as a plurality of acini and ducts 52 which couple Meibomian gland 50 to the surface of cornea 44. The eye shown also includes a lacrimal caruncle 54 as well as two canaliculi 56 which couple with a lacrimal sac 58 (also known as a tear sac) and a tear duct 60. Lacrimal gland 48 supplies an aqueous layer to the tear film whereas Meibomian gland 50 provides a lipid layer to the tear film via plurality of acini and ducts 52. Each time the eye blinks, when eyelid 42 moves downward in the direction of an arrow 62, the secretions of lacrimal gland 48 and Meibomian gland 50 which form the tear film, spread across cornea 44 in the direction of an arrow 64 towards lacrimal caruncle 54. The liquid in the tear film empties into lacrimal sac 58 via canaliculi 56 and then drains via tear duct 60. Canaliculi 56, lacrimal sac 58 and tear duct 60 are under the skin and not normally visible.

The tear film covers the ocular surface. The functions of the tear film include nutrition of the ocular surface, lubrication of that surface and a chemical barrier to the outside environment. The tear film forms a layer that is about 8 μm thick and as mentioned above, is typically formed of three layers: an external or lipid layer, a central or aqueous layer and an inner or mucin layer. The tear film can also be considered more of a lipid boundary layer with aqueous phases incorporating differing concentrations of mucins throughout. Meibomian glands and the glands of Moll produce the lipid component of the tear film, including wax esters, triglycerides, free fatty acids, as well as neutral diesters. The lacrimal glands produce the aqueous component. Goblet cells, which are located in the conjunctiva, secret the mucin and contains membrane associated glycoproteins. The proteins contained in the tear film take part in other bodily processes, and for instance can function as antimicrobials, anti-inflammatories and also help in healing processes after trauma, besides offering mechanical protection to the surface of the cornea.

Human tears contain a complex of proteins that exert a tremendous influence on tear film stability and ocular surface integrity. At least 500 proteins have been identified in the tear film. These proteins, in turn, possess a range of functions, including bactericidal, virucidal and fungicidal activities, specific and non-specific immune capabilities and lipid transport abilities. Human tear proteins also minimize autolytic damage, attenuate ultraviolet B radiation induced effects, inhibit serine and cysteine proteases, promote ocular surface wound healing and modulate the proliferation, motility and differentiation of corneal and/or conjunctival epithelial cells. The source of these proteins is lacrimal glands, the ocular surface epithelium, the conjunctival blood vessels and the Meibomian gland as mentioned above.

Tears, which form the tear film, are secretions with the main function of lubricating and preventing the cornea from drying, flushing away foreign particles from the ocular surface, as well as distributing immunoglobulins (IgA and IgG) and antimicrobial proteins to the ocular surface in order to prevent infections. The cornea's innate immune system is comprised of many types of cells including epithelial cells, fibroblasts and Langerhans cells. Epithelial cells are in charge of the secretion of proteins such as TNF-α, IL-1, IL-6 and IL-8. The Meibomian gland is a large sebaceous gland, and sebaceous glands are known to secrete a variety of proteins, such as IgA and pro-inflammatory cytokines (for example, TNF-α and IL-1a) in non-ocular environments. In addition, the Meibomian gland secretes through a holocrine mechanism. Secretion occurs when mature epithelial cells lining the Meibomian ducts disintegrate and release their proteinaceous lipid contents into the ducts and onto the ocular surface.

Blepharitis is the general term for common ocular conditions characterized by inflammation, scaling, reddening and crusting of the eyelid. Blepharitis comes in a number of varieties and can be classified depending on the apparent source of the condition. Regardless, blepharitis in general is cause by either a bacterial infection in the eyelid, a blockage of the lacrimal gland which results in reduced lacrimal fluid production for the aqueous layer of the tear film or a blockage of the Meibomian gland which causes the aqueous layer of the tear film to evaporate due to an insufficient amount of sebum. In the case of insufficient supply of sebum to the eyes, blepharitis can be clinically referred to as dry eye syndrome (herein abbreviated as DES) and is characterized by a dysfunctional Meibomian gland. This condition can also be referred to as Meibomian gland dysfunction (herein abbreviated as MGD) and might be the result of the Meibomian gland not producing enough sebum, there being a blockage of the acini and/or ducts in the eyelid from the Meibomian gland to the surface of the eye or another abnormality in the Meibomian gland preventing it from secreting and producing sufficient amounts of sebum in the lipid layer of the tear film. Regardless of how MGD presents itself, the result is that the lipid layer of the tear film is lacking in sebum which leads to the tear film evaporating and causing DES.

Reference is now made to FIG. 1B, which is a schematic illustration of a cross section of a sample of epidermis, generally referenced 80, as is known in the prior art. Epidermis 80 is a stratified squamous epithelium, the main cells of which are called keratinocytes, which synthesize the protein keratin. Keratinocytes are in a constant state of transition from the deeper skin layers to the uppermost skin layer. Protein bridges called desmosomes connect keratinocytes. Epidermis 80 includes four separate layers formed by keratinocytes in various stages of keratin maturation. Moving from the outermost surface to the deeper layers, the four layers of the epidermis are: an outermost layer 82A, referred to herein as the stratum corneum 82A, a stratum granulosum 82B (also known as the granular cell layer), a stratum spinosum 82C (also known as the spinous or prickle cell layer) and a stratum basale 82D (also known as the basal or germinativum cell layer).

Stratum corneum 82A is made up of layers of hexagonal-shaped, non-viable cornified cells known as corneocytes. In most areas of the skin, there are 10-30 layers of stacked corneocytes. Each corneocyte is surrounded by a protein envelope and is filled with water-retaining keratin proteins. The cellular shape and orientation of the keratin proteins add strength to stratum corneum 82A. Surrounding the cells are stacked layers of lipid bilayers. The resulting structure of stratum corneum 82A provides the natural physical and water-retaining barrier of the skin. The upwards movement of epidermal cells, such as from stratum basale 82D to stratum corneum 82A usually takes about 28 days and is known as the epidermal transit time.

Methods and systems for treating blepharitis, including DES and MGD are known in the art. One common treatment includes controlling the environment a patient suffering from DES and MGD occupies their time in. This can include, for example, avoiding areas with smoke and dust, avoiding the use of hair dryers, heaters, air conditioners and fans, especially when such devices are directed toward the eyes, as well as the use of a humidifier to add moisture to a dry indoor environment. Another common treatment involves the manual application of lubricants to the eye to rehydrate it, such as the application of eye drops. A more involved treatment includes the application of anti-inflammatory medication to the eyelids to reduce inflammation of the Meibomian gland and ducts. Surgery can also be used in extreme cases to prevent the eyelid from fully opening, possibly leading to a reduction in tear film evaporation.

Heating systems have also been suggested as a method for unblocking the ducts of the Meibomian gland. For example, U.S. Pat. No. 9,510,972 to Badawi, assigned to Sight Sciences, Inc., is directed to a software-controlled device which can deliver targeted thermal energy to the Meibomian glands while allowing the eyelids to blink naturally. This dry eye treatment generally comprises a patch or strip affixed to the skin of the upper and/or lower eyelids to deliver heat or other forms of energy, pressure, drugs, moisture, etc. (alone or in combination) to either one or more Meibomian glands contained within the underlying skin. The treatment strip or strips include one or more strips configured to adhere to an underlying region of skin in proximity to one or both eyes of a subject such that the one or more strips allow for the subject to blink naturally without restriction from the patches. The strips are configured to emit energy to the underlying region of skin and are shaped to follow a location of the Meibomian glands contained within the underlying region of skin.

U.S. Pat. No. 8,083,787 to Korb et al., assigned to TearScience, Inc., is directed to a method of treating dry eye in humans wherein a flow of naturally occurring secretion to an eye is occluded due to a presence of an obstruction in a Meibomian gland in an eyelid. The method comprises the steps of lifting the eyelid away from the eye and softening the obstruction through an application of thermal energy to heat the obstruction to a temperature of between about 37° C. to about 47° C. The method further comprises the step of gripping the eyelid between a back plate and a force applicator such that a regulated force is applied to the eyelid to express the softened obstruction from the Meibomian gland.

Other systems and methods for treating MGD and DES can be found at https://tearscience.com/patents.

SUMMARY OF THE PRESENT DISCLOSED TECHNIQUE

It is an object of the disclosed technique to provide a novel method and system for the treatment of blepharitis, Meibomian gland dysfunction (MGD) and dry eye syndrome (DES) via actively inducing eye reflexes via the eyelids. Inducing the eye reflexes can be enhanced by the generation of skin tissue lesions. Optionally, heat can be applied as well to activate the inflammatory healing process of the eyelids.

In accordance with the disclosed technique, there is thus provided a dermal conditioning device for creating at least one pressure point in at least an external surface of an eyelid without tissue coagulation. The dermal conditioning device includes at least one skin tissue lesion generator, at least one controller, a power supply and a housing. The controller is coupled to with the skin tissue lesion generator, the power supply is coupled to with the skin tissue lesion generator and the controller. The housing encases the skin tissue lesion generator and the controller. The controller controls the skin tissue lesion generator to generate at least one signal and apply the signal to stress the external surface of an outer layer of the eyelid. The stress causes a formation of the pressure point on the eyelid without tissue coagulation, thereby activating at least one of a corneal reflex, a menace reflex and a lacrimation reflex of the eyelid by activating at least one nociceptor on the eyelid.

According to some embodiments of the disclosed technique, the skin tissue lesion generator includes at least one protrusion for generating at least one mechanical lesion on the external surface of the eyelid.

According to some embodiments of the disclosed technique, the controller controls the skin tissue lesion generator to additionally apply the signal to heat the external surface of the eyelid.

According to some embodiments of the disclosed technique, the dermal conditioning device generates a signal in which a distal end of the dermal conditioning device is at at least 37 degrees Celsius.

According to some embodiments of the disclosed technique, the dermal conditioning device generates a signal having a pulse of a duration ranging between 2 milliseconds and 60 milliseconds.

According to some embodiments of the disclosed technique, the controller controls the signal by controlling a first parameter of the signal. The first parameter may be selected from the group consisting of a timing, an intensity, a frequency, a duration and a phase of the signal. The first parameter may also be temperature if heat is additionally applied.

According to some embodiments of the disclosed technique, the skin tissue lesion generator includes a heat generator.

According to some embodiments of the disclosed technique, the skin tissue lesion generator includes a stress applying generator.

According to some embodiments of the disclosed technique, the skin tissue lesion generator includes an actuator, mechanically coupled to a distal end of the dermal conditioning device and configured to apply the signal to stress the external surface of the eyelid.

According to some embodiments of the disclosed technique, the dermal conditioning device further includes a position sensor, coupled with the skin tissue lesion generator, for determining a depth of at least one protrusion into the external surface of the eyelid.

In accordance with another aspect of the disclosed technique, there is thus provided a method for creating at least one pressure point on at least an external surface of an eyelid. The method includes the procedures of generating at least one pressure point on the external surface of at least one eyelid epidermis. The method also includes the procedures of continuously generating the pressure point until at least one of tearing reflex, a hand-blink reflex and a blinking reflex occur in the eyelid thereby reinitiating the functionality of at least one of a Meibomian gland and a lacrimal gland.

According to some embodiments, the pressure point generates at least one lesion, the lesion having a depth ranging between 5% to 90% depth of a thickness of the eyelid epidermis.

According to some embodiments of the disclosed technique, the method further includes the procedure of activating an immune system response of the eyelid thereby further reinitiating the functionality of the Meibomian gland and the lacrimal gland.

BRIEF DESCRIPTION OF THE DRAWINGS

The disclosed technique will be understood and appreciated more fully from the following detailed description taken in conjunction with the drawings in which:

FIGS. 6A-6B are schematic illustrations of a dermal conditioning device of the disclosed technique that produces heat using an RF emitter, constructed and operative in accordance with another embodiment of the disclosed technique;

DETAILED DESCRIPTION OF THE EMBODIMENTS

Figure 1A:
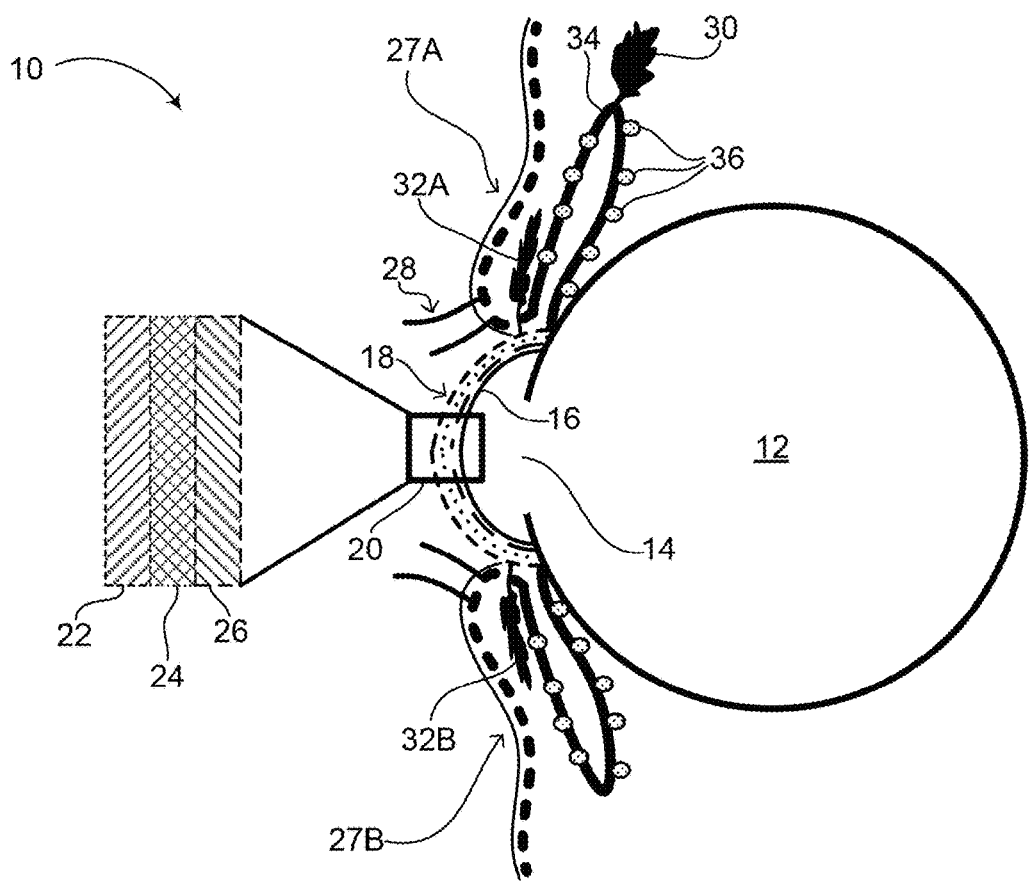
FIG. 1A shows schematic illustrations of the eye showing the organs involved in tear film production, as is known in the prior art.
Figure 1A:
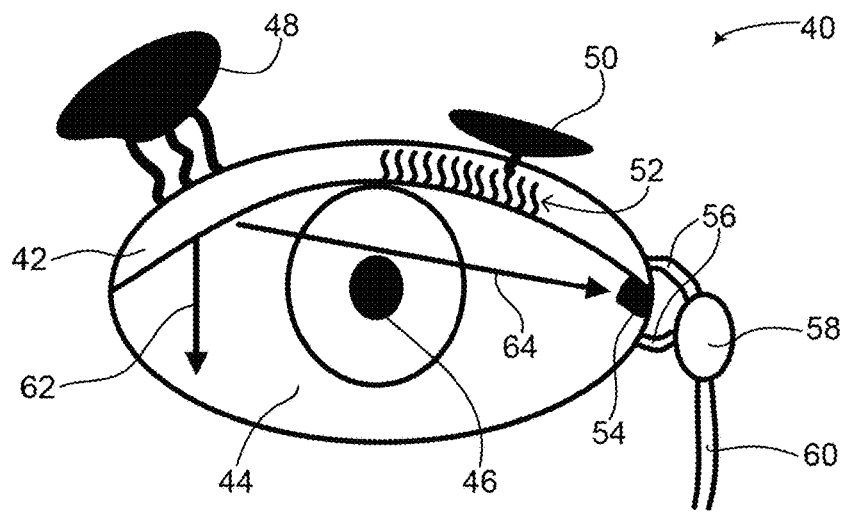

The disclosed technique overcomes the disadvantages of the prior art by providing a novel system, device and method for treating blepharitis and inducing eye reflexes via the eyelids thereby activating the Meibomian gland and the lacrimal gland for increasing sebum supply to the eye's tear film. In particular, the disclosed technique causes the corneal reflex to be activated as well as the lacrimation reflex and the menace reflex. The corneal reflex, also known as the blink reflex, is an involuntary blinking of the eyelids caused by stimulation of the cornea and can result from any external stimulus. The corneal reflex protects the eyes primarily from foreign bodies attempting to touch and enter the cornea. The lacrimation reflex, also known as the tear reflex, usually accompanied by the blink reflex, causes the involuntary production of tears in response to an irritant or foreign particle either in the eye or in the vicinity of the eye. The menace reflex, as known as the hand-blink reflex, is a blink reflex in response to the rapid motion of an object towards the eye. All of these reflexes cause the orbicularis muscle to activate, causing the eyelids to open and close rapidly (i.e., to blink) and thereby exerting substantial pressure on the Meibomian gland and the lacrimal gland. The system, device and method of the disclosed technique can further enhance the activation of the Meibomiam gland by an optional activation of the body's inflammatory healing process. The system and method of the disclosed technique uses a non-invasive and non-ablative process. According to the disclosed technique, sufficient pressure is applied to at least one eyelid of the eye (either the upper eyelid, the lower eyelid or both), i.e., at at least one pressure point, thereby directly activating nociceptors in the skin of the eyelid. The activation of nociceptors in the skin of the eyelid when sufficient pressure is applied also results in the activation of nociceptors on the cornea and sclera, thereby causing eye reflexes (i.e., at least one of the corneal, lacrimation and menace reflexes) to be activated which apply pressure to the Meibomian and lacrimal glands when the eye blinks as a result of the reflex. According to the disclosed technique, the pressure on the eyelid may also create tiny mechanical lesions on the eyelid epidermis in order to further activate at least one of the corneal, lacrimation and menace reflexes of the eye via the eyelids and also to activate the eye's immune system by excessive tear production in the lacrimal gland. The activation of these eye reflexes causes the orbicularis muscle to contract (i.e., flex) and relax, exerting pressure of the Meibomiam gland to secrete sebum and thereby resetting gland function by flushing out any blocked acini and ducts in the eyelid.

The orbicularis muscle is located on the outside of the tarsal plates in the eye. The orbicularis muscle itself can be subdivided into an orbital region that surrounds the eye and a palpebral region which forms the eyelid. The terminal or marginal end of the palpebral region, near the eyelid's end, includes the muscle of Riolan which encircles the terminal part of the Meibomian gland. When the orbicularis muscle contracts to cause an eye blink, the muscle of Riolan is also activated which aids in keeping the eyelids (when closed) in close apposition. The activation of both these muscles, the orbicularis muscle as well as the muscle of Riolan, may exert additional compression on the Meibomian gland to drive out any oil or debris in the acini, ducts and orifices of the Meibomian gland into the marginal lipid reservoir where it can eventually become part of the lipid layer of the tear film. Activation of the body's inflammatory healing process in the eye also activates the Meibomian gland to increase production of the sebum it normally produces which includes lipids and a combination of proteins in order to protect the corneal tear film from damage. The minimal pressure exerted as well as the optional non-permanent damage caused by the system and method of the disclosed technique to the eyelids and the eye is sufficient to cause the activation of at least one of the corneal, lacrimation and menace reflexes as well as to signal the immune system about a potential hazard to the cornea and thereby activate the release of pro-inflammatory proteins as well as other proteins related to the immune system which are generated by the lacrimal gland as a part of the healing process.

According to the disclosed technique, one method of activating the at least one of the corneal, lacrimation and menace reflexes besides also potentially activating the immune system of the eyelids is the activation of the nociceptors in the epidermis of the eyelid, which can also indirectly activate the nociceptors in the cornea and sclera by the pressure applied to the eyelid (for example at at least one pressure point). The system of disclosed technique can further exert pressure on the eyelid by generating tiny mechanical lesions in the eyelid. The pressure exerted by the disclosed technique on the eyelids, which translates into mechanical pressure and optionally tiny lesions on the eyelids, is what causes nociceptor activation on the eyelids and indirectly on the cornea and sclera. The pressure and the optional tiny mechanical lesions in the eyelid must be sufficient to cause the nociceptors in the epidermis of the eyelid and by extension the nociceptors in the cornea and sclera to react as if a foreign particle or object is entering the eye, in the vicinity of the eye or as if an object is moving rapidly towards the eye to cause the central nervous system to initiate the corneal reflex, the lacrimation reflex and/or the menace reflex. Activation of the nociceptors does not generate high levels of pain during the impact on the eyelids by the disclosed technique. The disclosed technique can further be used to generate tiny mechanical lesions on the eyelid however without causing tissue coagulation.

According to the disclosed technique, a dermal conditioning device is provided which includes at least one non-invasive eyelid epidermis and/or epidermis/dermis mechanical lesion generator, at least one controller, a power supply and a housing. A controller is used to control the mechanical lesion generator for exerting pressure on the eyelids, and optionally for making tiny lesions on the eyelids which do not cause significant pain (thus not causing tissue coagulation), do not cause any permanent damage to the eyelids (including the skin of the eyelids) or to the eye, the cornea or the sclera yet do induce at least one of the corneal, lacrimation and menace reflexes and optionally also the inflammatory healing process of the eyelid skin which heals the damaged epidermis of the eyelids. The activation of the above mentioned eye reflexes provide relief for DES and MGD by exerting compression on the Meibomian gland by the orbicularis muscle during blinking and results in the secretion of sebum from the gland. The activation of the inflammatory healing process of the skin (for example, due to the generation of tiny lesions on the eyelid) which also heals the damaged epidermis and dermis of the eyelids can provide additional relief for DES and MGD. The inflammatory healing process can be further activated by the activation of thermal nociceptors on the eyelids by the optional application of heat to the eyelids by the disclosed technique. The amount of mechanical stress and heat applied to the eyelids using the disclosed technique may influence how long the above mentioned reflexes occur (meaning an increase in the activation of the orbicularis muscle and muscle of Riolan) as well as the length of time the inflammatory healing process of the body is specifically active in the eyelids. An increase in the amount of mechanical stress and/or heat applied to the eyelids, which may also cause a slight increase in pain, may provide enhanced relief for DES and MGD (up to a degree). According to the disclosed technique, the amount of mechanical stress and/or heat applied should not go beyond the limit where pain is indicative of possibly permanent damage to the eyelids. The application of heat may induce slight tissue coagulation due to the activation of thermal nociceptors in the eyelids which may further enhance the treatment of DES and MGD due to increased blinking of the eye.

It is thus important to note that the disclosed technique activates nociceptors in the eyelid as well as the eye in order to treat DES and MGD without ever touching the eye. The device and system of the disclosed technique achieves this activation through a carefully controlled mechanism which can apply stress and optionally heat such that damage or injury to the eye itself (for example, the sclera and/or cornea) is prevented during treatment. In addition, even if application of the device and system of the disclosed technique increases the intraocular pressure in the eye, any change in intraocular pressure is transient and short-lived thereby preventing damage to the retina and optic nerve. According to the disclosed technique, typical treatment and use of the device may be between a few seconds to a few minutes per eye, thus avoiding any prolonged increase in intraocular pressure.

According to the disclosed technique a system and method is provided wherein the skin of the eyelid, where the lacrimal gland and the Meibomian gland are situated, undergoes mechanical stress and optionally small mechanical lesions, for example between 50-700 microns deep or between 20-1000 microns deep. The thickness of the eyelids ranges between 800-1500 microns deep. According to the disclosed techniques, lesions may be formed having a depth of between 5%-90% of the thickness of the eyelids, for example between 20-1000 microns. A depth of 20 microns into the eyelids is substantially the start of the viable epidermis (i.e., midway into the stratum corneum) whereas a depth of 1000 microns into the eyelids is deep into the dermis and borders on the threshold of significant pain if further penetrated. The lesions can be formed by using strain or by mechanical force. The lesions can also be formed by additionally using heat. The disclosed technique thus causes an epidermal lesion, similar to a burn, on the eyelid without causing coagulation of the skin tissue however resulting in a relatively long period of slight pain and irritation that may last approximately between 1 to 144 hours (i.e., short lived slight pain or slight pain for a few days) post treatment. In one embodiment of the disclosed technique, increased heat can be used which may cause slight tissue coagulation and due to the activation of thermal nociceptors in the eyelids, may enhance the relief of DES and MGD provided to the eyelids by causing additional blinking reflexes due to the pain resulting from the slight burn caused by the applied heat. In this embodiment as well, the pain may last between 1 to 144 hours. The strain and/or mechanical force applied to the eyelid by the disclosed technique causes the activation of the corneal, menace and lacrimation reflexes as well as an epidermal lesion. These reflexes cause the eye to blink and to exert pressure on the Meibomian gland, for example from the contraction of the muscle of Riolan. The epidermal lesion also activates the body's natural inflammatory healing process which induces the activation of epidermal growth factor (herein abbreviated EGF) in the Meibomian gland acini and ducts thus leading to regeneration of the gland's functioning. At the same time, the epidermal lesion along with the strain and/or mechanical force applied is insufficient to change the viscosity of the sebum of the tear film.

This is due to the working range of the dermal conditioning device of the disclosed technique, including the parameters relating to intensity, time, force, depth and the like and that the strain and/or mechanical force applied to the eyelids is applied in a transient manner to prevent any permanent damage to the eyelids, including changing the viscosity of the sebum of the tear film.

It is noted that medical models which explain the mechanism of DES show EGF and other tear film components, such as proteins, vitamins (like vitamin A), other growth factors and hormones, working in a closed-loop control system governed by the lacrimal gland. Balancing of the chemical composition of the tear film by the lacrimal gland enables controlling the behavior and functioning of the Meibomian gland. For example, an increase in vitamin A in the chemical composition of the tear film by the lacrimal gland will result in a reduced secretion of sebum by the Meibomian gland. Conversely, a reducing in vitamin A in the chemical composition of the tear film by the lacrimal gland will result in an increased secretion of sebum by the Meibomian gland as well as an increase in the amount of EGF.

The corneal reflex, the menace reflex and the lacrimation reflex cause the orbicularis muscle (including the muscle of Riolan) to contract and relax, thereby causing the eye to blink causing lacrimal fluid to spread across the exposed sclera and cornea of the eye. The contraction of the orbicularis muscle also exerts physical pressure on the lacrimal gland and the Meibomian gland, thus causing them to excrete lacrimal fluid, sebum and meibum. According to the disclosed technique, by actively inducing the corneal reflex, menace reflex and the lacrimation reflex, the pressure exerted by the contraction and relaxation of the orbicularis muscle causes orifices, acini and ducts in both glands' to be flushed out, thereby cleaning any blocked ducts, resetting gland function and providing treatment for DES and MGD.

Reflex tearing (or the lacrimation reflex as amended above) in the body is produced by strong physical or emotional stimulation of the lacrimal gland. The tears thus produced contain essential components, such as vitamin A and EGF, for the proliferation and differentiation of the corneal and conjunctival epithelium. Even when basic tearing is decreased, such as during DES and/or MGD, accelerating desiccation of the ocular surface, if reflex tears are present, they can provide the ocular surface epithelium with substances necessary for proper epithelial wound healing. According to the disclosed technique, the generation of mechanical lesions in the eyelids additionally causes the same reaction of the body in reflex tearing. Reflex tearing leads to blinking which is the mechanism by which the tear film is spread over the ocular surface. By slightly damaging the eyelids using the disclosed technique, eye reflexes are activated and an inflammatory healing process occurs in the epidermis and dermis of the eyelids. In this process, the lacrimal glands produce many proteins, as mentioned above, including an increase in EGF. Tear production of EGF has a strong effect on the functioning of the Meibomian gland and according to the disclosed technique, the production of EGF in the lacrimal gland leads to an inflammatory healing process in the Meibomian gland that can treat MGD as well as DES.

According to the disclosed technique, the corneal reflex, the menace reflex, the lacrimation reflex and the increased presence of EGF in the eyelid induces the Meibomian gland to secrete more meibum and sebum thereby cleaning any blocked acini and ducts and relieving the symptoms of MGD and DES. The presence of EGF has been shown to restore proper functionality of the Meibomian gland including proper production and secretion of meibum and cleansing of the acini and ducts. The disclosed technique thus induces the lacrimal glands and Meibomian glands to produce more meibum and sebum and enables a non-invasive and non-ablative treatment for MGD and DES. According to the disclosed technique, pressure can be exerted either on the lower eyelid while the eye stays open, on the upper eyelid while the eye is closed or on both the lower and upper eyelids while the eye is closed. The application of pressure to the lower eyelid by the disclosed technique is sufficient to activate the menace reflex (besides the corneal reflex and the lacrimation reflex). As mentioned above, the amount of pressure exerted is controlled and is sufficient to activate nociceptors in the eyelid and the eye while also not significantly affecting the intraocular pressure (which could damage the retina and optic nerve). This is partially achieved by limiting treatment time of the disclosed technique from a few seconds to a few minutes at most. This is also achieved by precisely controlling the depth (at the magnitude of microns) to which elements of the device and system of the disclosed technique can depress into the eyelids. Optionally this is further achieved by precisely controlling parameters relating to the amount of heat provided to the eyelids, including the amount of contact time between a heated element and the eyelids. When the eye remains open, as the device and system of the disclosed technique moves over the lower eyelid, the movement mechanism of the disclosed technique is perceived by the eye as a potential hazard and thereby activates the menace reflex, the blinking reflex and the tear reflex. In one embodiment, perception of the movement of the device and system of the disclosed technique by the eye may be enhanced by manufacturing certain elements of the disclosed technique from a transparent material, as described below. In addition, even though the eye may generally remain open while the disclosed technique is in use, the movement of the system of the disclosed technique is sufficient for the nociceptors in the eyelid to send a signal to the central nervous system to activate the menace reflex as if an object was moving rapidly towards the eye. According to the disclosed technique, in the embodiment where stress is applied to the eyelids and mechanical lesions are also formed, only the epidermis and/or dermis of the eyelids is subjected to lesions which are tiny and do not induce trauma. According to the disclosed technique it is required that the skin tissue of the eyelids not evaporate and remain intact. In one embodiment of the disclosed technique, a sufficient epidermal lesion is to be caused on the eyelids to activate the production of EGF. The inflammatory healing process of the body can thus repair the epidermis and dermis of the eyelid while also providing a treatment for MGD and DES.

The stratum corneum layer of the skin is capable of absorbing up to three times its weight in water and is pliable and flexible when hydrated, however when the water content drops sufficiently, the stratum corneum becomes brittle and is prone to cracking. This property is true of both humans and animals. In one embodiment of the disclosed technique this property is used to induce the inflammatory healing process of the skin of the eyelids while maintaining the cellular integrity and viability of the skin tissue of the eyelids. According to this embodiment of the disclosed technique, the epidermis and/or dermis is dehydrated sufficiently such that it becomes brittle. A stress (i.e., force per cross-sectional area) is then applied to the brittle stratum corneum, which causes a strain on the stratum corneum resulting in a lesion. The strain causes the formation of a plurality of lesions in the stratum corneum while not ablating it. The lesions induce the inflammatory healing process of the skin. Additionally, the lesions formed in the upper skin layers enable water to evaporate from the deeper skin layers in response to the continued application of heat to the external surface of the skin, i.e. the epidermis layer of the skin is dehydrated as well as part of the dermis layer, beneath the epidermis layer. This embodiment is an optional embodiment of the disclosed technique. This embodiment may cause slight tissue coagulation from the continued application of heat which may possibly enhance the relief provided by the disclosed technique to DES and MGD by activating thermal nociceptors in the eyelids leading to further blinking for an extended period of time.

The conditioning of the epidermis and/or dermis includes a stress-applying stage or a mechanical force generating stage that does not penetrate the skin, and is thus non-invasive. The conditioning of the epidermis and/or dermis may optionally include either a mechanical lesion forming stage, a heating stage or both. The heating stage causes dehydration of the skin, and the stress-applying stage causes a strain on the skin, resulting in a deformation of the surface of the skin and inducing the skin's natural healing process. The heating stage may also cause slight tissue coagulation leading to the activation of thermal nociceptors in the eyelids. For example, the amount of heat applied may be minimally 37° C. and upwards. Furthermore, the stress-applying stage may involve the use of an array of tiny needles which do not penetrate the epidermis. Optionally, the array of tiny needles can penetrate the skin to no more than between 20-1000 microns in a controlled and regulated manner, thus penetrating between 5%-90% of the minimal thickness of the eyelids. As mentioned above, 20 microns is the start of the viable epidermis (i.e., midway through the stratum corneum) of the eyelids whereas 1000 microns is deep into the dermis of the eyelids and at the border of where significant pain may be experienced by a patient if penetration goes beyond that depth. The stress is applied to cause just a sufficient amount of strain on the surface of the skin to cause the formation of fissures without inducing trauma. Thus, in contrast to conventional prior art techniques, the disclosed non-ablative technique results in minimal coagulation or denaturation of the skin cells. The optional tissue coagulation stage and the non-invasive, strain-applying stage may be applied sequentially, in tandem or as a combination thereof. In addition, unlike known prior art techniques, the disclosed technique causes repairable skin damage without permanent damage to the skin while also providing treatment for DES and MGD.

It is noted as well that the disclosed technique is described in reference to a human eye and the treating of blepharitis in humans.

Figure 2A:
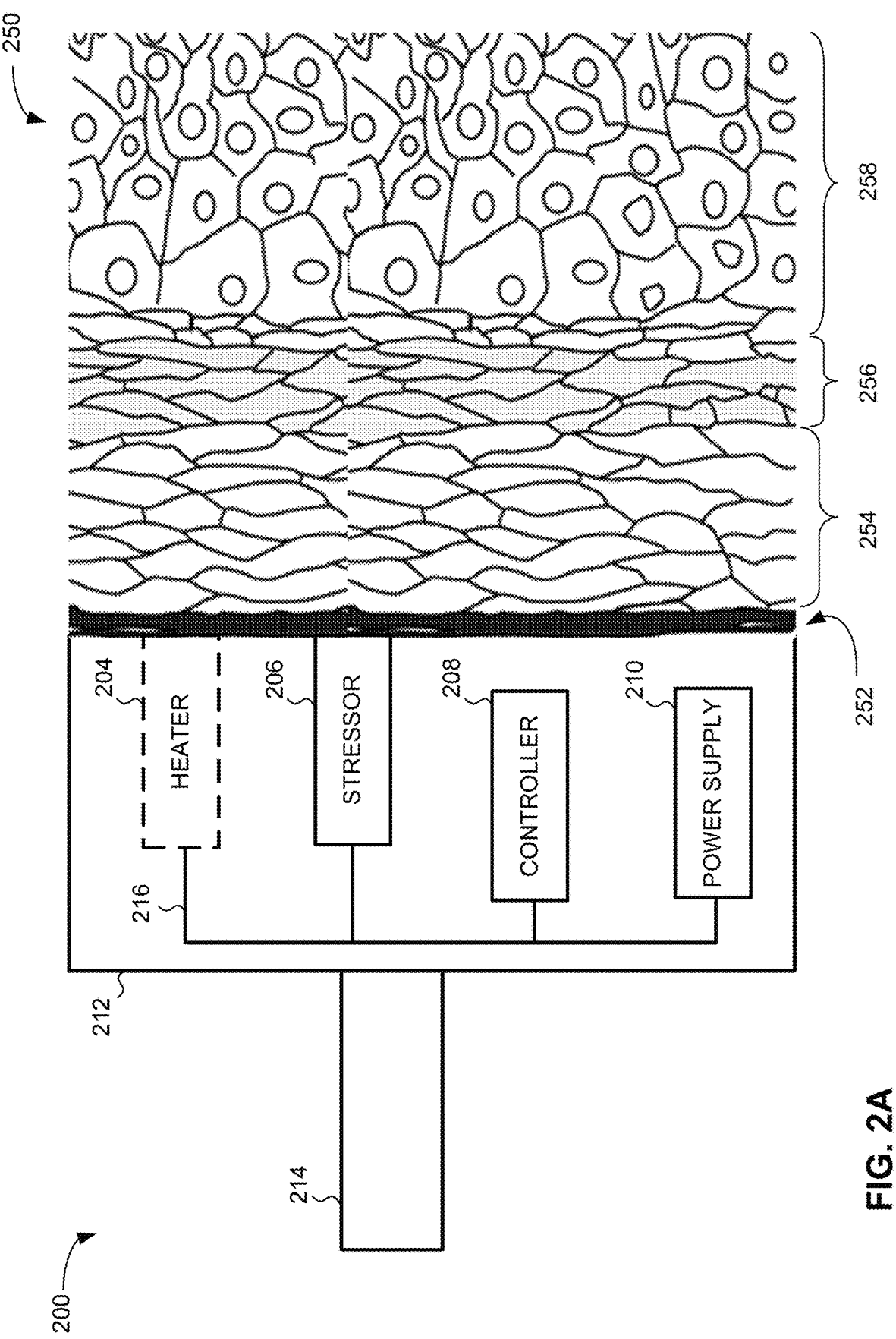
FIGS. 2A-2C are schematic illustrations of a dermal conditioning device constructed and operative in accordance with an embodiment of the disclosed technique.
Figure 2B:
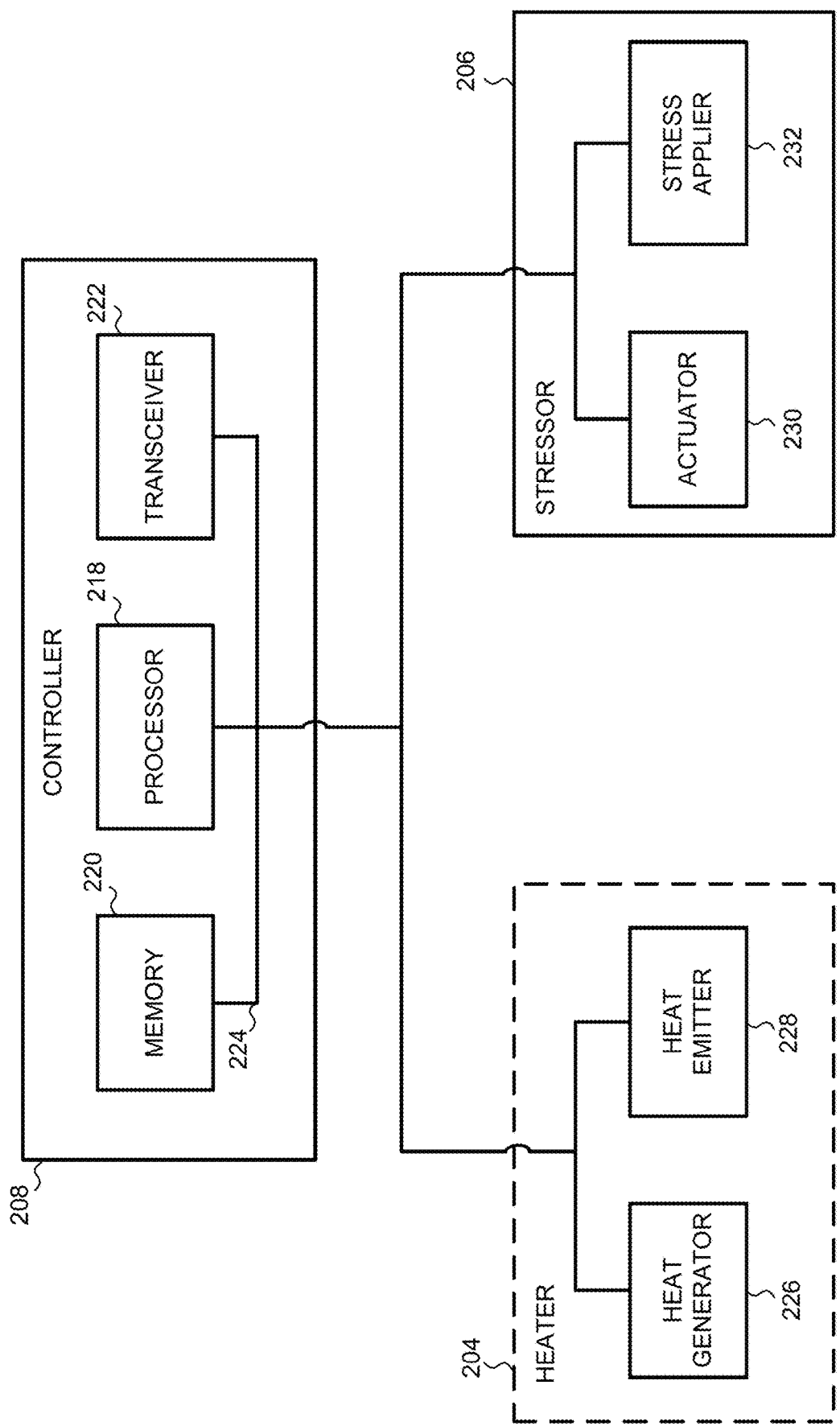

Reference is now made to FIGS. 2A-2B, which are schematic illustrations of the dermal conditioning device, generally referenced 200, constructed and operative in accordance with an embodiment of the disclosed technique. With reference to FIG. 2A, dermal conditioning device 200 is shown positioned in proximity to an area of skin 250. The layers of area of skin 250 are indicated as a stratum corneum layer 252, a stratum granulosum 254, a stratum spinosum 256 and a stratum basale 258. Stratum granulosum 254, stratum spinosum 256 and stratum basale 258 can collectively be referred to as deeper skin layers. FIG. 2A shows area of skin 250 prior to conditioning by dermal conditioning device 200, with stratum corneum layer 252 fully intact.

Dermal conditioning device 200 includes a stressor 206, a controller 208 and a power supply 210, all enclosed within a housing 212. Dermal conditioning device 200 also optionally includes a heater 204. Attached to housing 212 is a handle 214. Stressor 206, controller 208 and power supply 210 are each electrically coupled to each other via a communications bus 216 that transfers data therebetween, using known techniques, including any of wired, optical fiber and software (e.g. communications protocols) channels. Heater 204, if used, is also electrically coupled to the other elements in housing 212 via communications bus 216. Communications bus 216 may transfer data serially, in parallel or in a combination thereof. Stressor 206 generates a stress for applying to area of skin 250, in accordance with one or more stress control parameters as determined by controller 208. The stress may be a mechanical stress, pressure exerted by air flow, a mechanical force and the like. Stressor 206 is coupled to the distal end of dermal conditioning device 200 such that the stress produced by stressor 206 is applied to area of skin 250 when positioned in sufficient proximity to the distal end of dermal conditioning device 200. The applied stress produces a strain on area of skin 250, and can optionally resulting in the formation of a plurality of fissures or lesions. The applied stress also produces the corneal, menace and lacrimation reflexes of the orbicularis muscle (not shown) beyond stratum basale 258 of skin 250. Stressor 206 can be considered a mechanical lesion generator for applying pressure and also for optionally generating lesions in skin tissue, for example in the eyelids. As mentioned above, housing 212 may be made from a transparent material (such as a transparent plastic), thereby enabling the area of skin 250, for example in the case of a lower eyelid, to perceive movement of dermal conditioning device 200, thereby enhancing the activation of the menace reflex and the corneal reflex.

As mentioned above, optionally heater 204 generates heat for coagulating area of skin 250, in accordance with one or more heat control parameters as determined by controller 208. Heater 204 is thermally coupled to the distal end of dermal conditioning device 200 such that heat produced by heater 204 is delivered to area of skin 250 when positioned in sufficient proximity to the distal end of dermal conditioning device 200. The delivered heat causes water to evaporate from area of skin 250. In this embodiment, heater 204 and stressor 206 can be considered a mechanical lesion generator for generating lesions in skin tissue, for example in the eyelids.

As illustrated in FIG. 2A, prior to conditioning skin 250 by dermal conditioning device 200, stratum corneum layer 252 of the area of skin 250 is smooth and fully intact, having no significant fissures. In this state, stratum corneum layer 252 poses a barrier between deeper skin layers 254, 256, and 258 and the external surface of stratum corneum layer 252 facing the distal end of dermal conditioning device 200. Thus, stratum corneum layer 252 prevents the viable cells within deeper skin layers 254, 256, and 258 from absorbing an externally applied solution.

Reference is now made to FIG. 2B which is a schematic block diagram of controller 208 and stressor 206 of FIG. 2A, as well as optional heater 204 (FIG. 2A), constructed and operative in accordance with an embodiment of the disclosed technique. Controller 208 includes at least one processor 218, a memory 220, a transceiver 222 and a communications bus 224. Processor 218, memory 220 and transceiver 222 are electrically coupled to each other via communications bus 224. Communications bus 224 transfers data using known techniques, including any of wired, optical fiber and software (e.g. communications protocols) channels. Communications bus 224 may transfer data serially, in parallel or in a combination thereof. Transceiver 222 receives data via any known communications means, wired, wireless or both, such as through infrared technology, Bluetooth® technology, Ethernet technology and the like. The data may include one or more program code instructions, one or more parameters for controlling the operation of dermal conditioning device 200 and the like. Memory 220 is a computer readable media operative to store the one or more program code instructions, data and operational parameters. Processor 218 applies the parameters when executing the one or more program code instructions to control the operation of dermal conditioning device 200, such as to control the operation of heater 204, stressor 206 or both of FIG. 2A.

Controller 208 controls the operation of heater 204 and stressor 206 to apply the respective heat and strain to area of skin 250 either sequentially, simultaneously or a combination thereof. For example, controller 208 may first control the implementation of the dehydrating stage by heater 204 and then control the implementation of the stress-applying and strain-producing stage by stressor 206. In another embodiment, controller 208 may synchronize the operation of heater 204 and stressor 206 such that the dehydrating stage and stress-applying and strain-producing stage are implemented simultaneously. Heater 204 and stressor 206 can work together to generate epidermal lesions on the skin tissue of the eyelids. The lesions can be mechanical lesions or small burns to the eyelids.

Heater 204 includes a heat generator 224 and a heat emitter 226. Heat generator 224 is electrically coupled to controller 208 and power supply 210 (FIG. 2A). Heat emitter 226 is thermally coupled to heat generator 224 and to the distal end of dermal conditioning device 200 (FIG. 2A). Heat generator 224 generates heat in accordance with one or more heat control parameters, such as temperature (in degrees Celsius—° C.), wavelength (in nanometers—nm), energy level (in Joules—J), timing (in seconds) and the like. Controller 208 controls the operation of heat generator 224 in accordance with the heat control parameters. Heat emitter 226 emits the heat generated by heat generator 224 from the distal end of dermal conditioning device 200 onto area of skin 250, when area of skin 250 is positioned in proximity to the distal end of dermal conditioning device 200. Controller 208 controls the generation of heat by heat generator 224 and the emission of heat by heat emitter 226 to cause the dehydration of area of skin 250, such that the water content of stratum corneum layer 252 is less than 10% and the water content of stratum granulosum 254 is less than 70%. For example, controller 208 controls any of the timing, frequency, temperature and intensity of the heat emitted by heat emitter 226. Controller 208 may receive feedback regarding the state of area of skin 250 from one or more sensors (not shown), and adjust the generation of heat by heat generator 224 and the emission of heat by heat emitter 226, accordingly.

In accordance with the disclosed technique, the following formulae are used to determine the parameters for operating heater 204. For a constant heat capacity, the amount of energy required to evaporate water may be calculated as:

Energy = (mass) × (temperarture difference) × (specific heat capacity)  (1)

Even though live skin tissue does not have a constant heat capacity, over fairly narrow temperature ranges below 100° C. the variations in the heat capacity for skin tissue are fairly small and errors resulting from assuming a constant heat capacity are correspondingly small. For example, at atmospheric pressure, the specific heat capacity at constant pressure changes from 4.183 kJ/(kg·K) at 20° C. to 4.194 kJ/(kg·K) at 80° C., a change of only 0.3%. For other substances, such as superheated water, the variation in heat capacity with respect to temperature and pressure may be significant. At 350° C. (200 bar) the heat capacity is 8.138 kJ/(kg·K), nearly twice the heat capacity at 20° C. at the same pressure. The amount of heat required to evaporate water from live skin tissue can thus be calculated as the sum of the sensible heat ($Q_{sh}$) and the latent heat ($Q_{lh}$). Sensible heat in the context of the disclosed technique relates to the heat required to heat a tissue such that its surface temperature (usually 32° C.) is approximately 100° C. Latent heat is the heat required to change the state of heated water from liquid to vapor. Therefore the required heat, $Q_{Th}$, is given by the sum of the sensible heat and the latent heat as follows:

$$Q_{Th} = Q_{sh} + Q_{lh} \qquad (2)$$

The sensible heat is calculated as the specific heat capacity of water, multiplied by the temperature change. The latent heat is calculated as the specific latent heat for water multiplied by the amount of water, measured as the mass of the water. Thus the required heat may be rewritten as:

$$Q_{Th} = C_m(T_2 - T_1) + mL \qquad (3)$$

where L is the specific latent heat (for water this is 2264.76 kJ/(kg·K)), m is the mass (kg), $C_m$ is the specific heat capacity of water (4.2 kJ/(kg·K)), $T_2$ is the final temperature (° C.) of the skin and $T_1$ is the initial temperature (° C.) of the skin. Direct heat transfer (flow) from the distal end of dermal conditioning device 200 to the different layers of skin 250 may be determined by the following general equation:

$$\text{heat flow} = \frac{\text{Thermal potential difference}}{\text{Thermal resistance}} \qquad (4)$$

More specifically, the thermal potential difference is given by the temperature differential, $T_i - T_j$, multiplied by the heat conductivity, k, and the thermal conductive area, A, and the thermal resistance is given by the thickness of the skin. Thus the direct heat transfer is determined by the following more specific equation:

$$q = -k_a A \frac{T_2 - T_1}{\Delta x_a} = -k_b A \frac{T_3 - T_2}{\Delta x_b} \qquad (5)$$

where q is the heat flow, $T_i - T_{i-1}$ is the temperature difference within each skin layer, $\Delta x_a$, $\Delta x_b$ are the thicknesses for skin layers a and b, A is the thermal conductivity area of the skin, and $k_a$, $k_b$ are the heat conductivity for skin layers a and b, respectively.

The amount of heat absorbed by area of skin 250 is a function of the distance between heat emitter 228, positioned at the distal end of dermal conditioning device 200 and the thermal properties of skin 250. Since skin 250 is considerably large as compared to the distal tip of dermal conditioning device 200, the distal tip of dermal conditioning device 200 may be analyzed as a lumped mass. In a lumped mass the interior temperature remains essentially uniform throughout the heat transfer process and the temperature (T) can be taken to be a function of just time (t), thus giving T(t). The heat transfer for a lumped mass model is the heat transferred into area of skin 250 over a time interval dt, which equals to the increase in the energy of area of skin 250 during the time interval dt and can be expressed mathematically as the product of the heat transfer coefficient (h) over the contact area ($A_s$) of dermal conditioning device 200 with area of skin 250, multiplied by the temperature difference ($T_\infty - T$) over time period dt. This is equivalent to the mass (m) of the treated area of skin 250 multiplied by the specific heat $c_p$ of skin 250 and can be expressed as the following formula:

$$hA_s(T_\infty - T)dt = mc_p dT \quad (6)$$

where h is the heat transfer coefficient (W/(m²·K)), $A_s$ is the contact area of dermal conditioning device 200 with the treated area of skin 250, $T_\infty$ is the final temperature of area of skin 250 (° C.), T is the initial temperature of area of skin 250 (° C.), m is the mass (kg) of the treated area of skin 250 and $c_p$ is the specific heat of area of skin 250 (Kg·m²/(K·s²)). Noting that m=ρV with ρ being the density of area of skin 250 (kg/m³), V being the volume (m³) of the treated area of skin 250, equation (5) may be rewritten as:

$$\frac{d(T - T_\infty)}{T - T_\infty} = \frac{hA_s}{\rho V c_p} dt \quad (7)$$

which can be solved, as follows:

$$\frac{T(t) - T_\infty}{T_i - T_\infty} = e^{-bt} \quad (8)$$

where $$b = \frac{hA_s}{\rho V c_p} \quad (9)$$

Heat generator 226 may be implemented using any known technique for generating heat, as per the following examples:
  Heat generator 226 may be a mechanical heat generator that heats via friction;
  Heat generator 226 may be a heat generating element that is thermally coupled to a heat conducting element forming heat emitter 228, disposed at the distal end of dermal conditioning device 200;
  Heat generator 226 may be a heat generating element coupled to an air pressurizer that is fluidly coupled to the distal end of dermal conditioning device 200 via multiple air channels forming heat emitter 228;
  Heat generator 226 may be an infrared (herein IR) or near IR laser emitter optically coupled to heat emitter 228, configured as a plurality of fiber optic channels disposed at the distal end of dermal conditioning device 200; and
  Heat generator 226 may be an RF signal emitter electrically coupled to heat emitter 228, configured to channel the RF signal from the distal end of dermal conditioning device 200.

Regardless of how the heat is generated, the amount of heat generated is applied in a transient manner (i.e., not continuously) such as to not distort or permanently damage the skin tissue of the eyelids. This is achieved by applying the heat intermittently depending on how the heat is generated. In the case of heat being transferred via radiation (like in the case of a laser or an RF signal), the pulse repetition rate (for example between 2-60 ms) is such that each individual pulse does not distort the skin tissue yet is sufficiently strong to create a skin tissue lesion. In the case of heat being transferred via convection or conduction, the heat is applied transiently to the eyelids, either via an on-off switching (such as with pressurized air) or via an advancing and retracting (such as with heated elements) of the elements with the skin (again, for example, with a pulse rate of between 2-60 ms). The above description regarding heater 204, as described above, represents an embodiment of the disclosed technique wherein heat is applied to skin tissue of the eyelids besides the application of a mechanical stress or force. However the disclosed technique does not require heat to function and can be achieved by only the application of mechanical stress or force to the skin tissue of the eyelids as described below.

Stressor 206 includes an actuator 230 and a stress applier 232. Actuator 230 and stress applier 232 are coupled to each other such that a force actuated by actuator 230 is conveyed by stress applier 232 onto area of skin 250 when area of skin 250 is positioned in sufficient proximity to the distal end of dermal conditioning device 200. For example, actuator 230 may be mechanically coupled, electrically coupled or fluidly coupled to stress conveyor 232. Exemplary embodiments are described in greater detail below in FIG. 5A-5E, however these examples are not intended to be limiting. Actuator 230 is electrically coupled to controller 208 and power supply 210 (FIG. 2A). Actuator 230 generates a stress in accordance with one or more stress control parameters, such as force (in Newtons—N), energy level (in Joules—J), frequency (in hertz—Hz), phase (in seconds), timing (in seconds) and the like. Actuator 230 may be any known stress actuator, such as a an electric motor (for example, a brushed DC motor, a brushless DC motor, a linear motor and the like), a piezoelectric element, an RF emitter and the like, embodiments of which are described in greater detail below in FIGS. 6A-6B. Actuator 230 may also be embodied as any kind of piston or actuator, such as a hydraulic piston, a pneumatic piston, a magnetic piston, a piezoelectric piston, a solenoid actuator (for example, a linear solenoid actuator, a rotary solenoid actuator and the like), a voice coil actuator and the like. In some embodiments of the disclosed technique, actuator 230 can be any kind of piston or actuator for moving elements precisely over small distances. Controller 208 controls the operation of actuator 230 in accordance with the stress control parameters mentioned above. Stress applier 232 conveys the stress generated by actuator 230 from the distal end of dermal conditioning device 200 onto area of skin 250. In response to the applied stress, a strain is produced on area of skin 250, resulting in the formation of a plurality of lesions. The depth to which stress applier 232 extends into area of skin 250 is controlled by controller 208, which may additionally include a motion controller (not shown). Stressor 206 can also include a position sensor (not shown) for determining a depth to which stress applier 232 has extended into area of skin 250. The position sensor may be embodied as an encoder (such as a magnetic encoder, an optical encoder and the like) or as a Hall effect sensor (either analog or digital). As mentioned above, the dermal conditioning device of FIGS. 2A and 2B can be used on the upper eyelid when the eyes are closed, on the lower eyelid when the eyes are open or on both eyelids (upper and lower) when the eyes are closed.

Figure 2C:
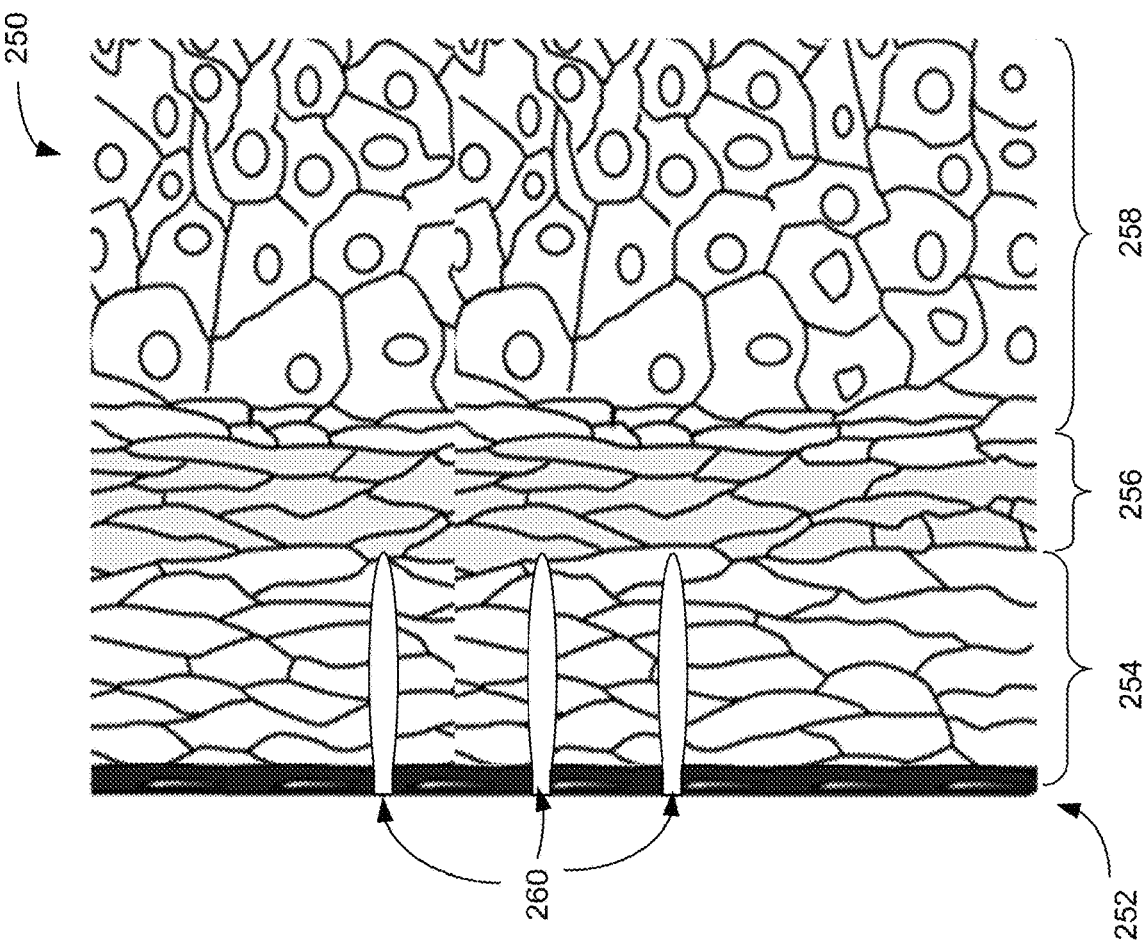
Figure 2C:
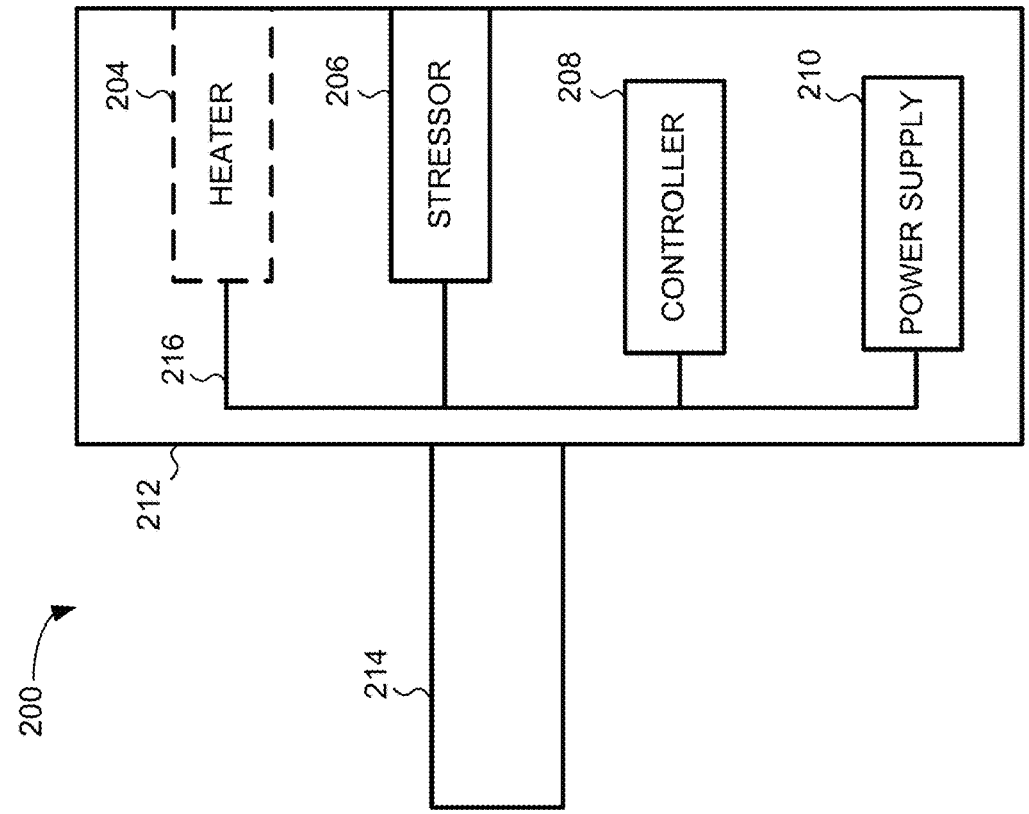

With reference to FIG. 2C, dermal conditioning device 200 is shown in proximity to area of skin 250 after treatment by dermal condition device 200. Area of skin 250 is slightly damaged, presenting a plurality of lesions 260 within dehydrated stratum corneum layer 252 and reaching down into the first of the deeper skin layers 254. Stratum corneum layer 252 may be thinner after treatment by dermal condition device 200 than prior to treatment. Plurality of lesions 260 are caused by the strain produced on skin 250 as a result of the stress applied by stress applier 232. Plurality of lesions 260 can be enhanced by the additional application of heat applied by heat emitter 228. Each of plurality of lesions 260 provides sufficient damage that thermal nociceptors report enough pain to the central nervous system to trigger the body's inflammatory healing process in the eyelids yet not so much so that significant tissue coagulation occurs. Notably, the cellular structure within stratum corneum layer 252 and deeper skin layers 254, 256, and 258 after the conditioning by dermal conditioning device 200 remain generally intact thereby exhibiting minimal trauma. In the case of application to the eyelids, the cellular structure of the stratum corneum layer and the deeper skin layers exhibit sufficient structural change to induce the body's healing process thus resulting in the production of EGF which aids in treating DES and MGD. The applied stress on the eyelids of the disclosed technique is sufficient to indirectly cause corneal and scleral nociceptors to report the possibility of foreign objects or particles near the eye or moving rapidly towards the eye, thus causing the central nervous system to trigger any one of the corneal reflex, the menace reflex and the lacrimation reflex. As mentioned above, this can be achieved by stressor 206 without the creating of tiny lesions but merely with pressure exerted on either the lower eyelid, upper eyelid or both. Stressor 206 can additionally cause tiny lesions in the eyelids, thereby further activating the above mentioned reflexes and also causing the inflammatory healing process of the eyelids to activate. The inflammatory healing process can further be activated by optionally applying heat to the eyelids by heater 204. Stressor 206 thus activates nociceptors in the eyelids and the eye to treat DES and MGD without touching the eye itself. Stressor 206 may be applied to an eyelid on different locations to cover an external surface of the eyelid ranging between 10%-80% of the total outer surface of the eyelid. Stressor 206 may generate a sequence of pulses for a total time period ranging between 1-30 seconds, 1-4 minutes, 2-3 minutes or any other range of time from a few seconds to a few minutes. The application of stressor 206 to the eyelid is thus transient and short-lived (relatively speaking) thereby not causing any prolonged change in the intraocular pressure of the eye and preventing damage to the retina and/or optic nerve.

Controller 208 controls the conditioning of skin 250 indicated in FIGS. 2A and 2C by controlling heater 204 to produce sufficient heat to dehydrate the area of skin 250 without causing thermal damage to any of the surface or deeper layers of area of skin 250. Heater 204 produces heat and applies the heat to the external surface of stratum corneum layer 252 of skin 250, thereby causing water stored therein to evaporate. In one embodiment, controller 208 controls the temperature, intensity and timing of the heat produced by heater 204 to cause evaporation of water from the epidermal layers of skin 250 (e.g. stratum corneum layer 252 and deeper skin layers 254, 256, and 258) until the respective water content of stratum corneum layer 252 is less than about 10% and until the respective water content of the extracellular matrix (herein abbreviated ECM) of stratum granulosum 200B is less than about 70%.

Controller 208 also controls stressor 206 to produce a stress that, when applied externally to stratum corneum layer 252, causes a strain on stratum corneum layer 252, thereby activating the corneal, menace and lacrimation reflexes of the eye. In the case of optionally using heater 204, the stress produced by stressor 206 can additionally cause a strain on a dehydrated stratum corneum layer 252 which is sufficient to crack the dehydrated stratum corneum layer. Stressor 206 produces the stress and applies the stress to the external surface of stratum corneum layer 252 without penetrating stratum corneum layer 252. Stressor 206 can also produce a stress which penetrates the external surface of the stratum corneum layer, causing the formation of plurality of lesions 260 and triggering an immune response. Thus the conditioning of skin 250 by dermal conditioning device 200 is non-invasive or minimally-invasive. The size and depth of plurality of lesions 260 may range from 20 to 1000 microns in depth and may have a diameter at most of about 700 microns. The depth mentioned corresponds to about 5%-90% of the minimal thickness of the skin tissue of the eyelids. The ratio of lesioned tissue to non-lesioned tissue in the conditioned stratum corneum layer 252 may range between 1% and 30%. The ratio may be, for example, the ratio of the width of plurality of lesions 260 to the width of the intact regions of stratum corneum layer 252. In another embodiment of the disclosed technique stressor 206 may be embodied as a plurality of heated tips which can be advanced and retracted into skin 250. In this embodiment, the plurality of heated tips is used to puncture the stratum corneum and the stratum granulosum up to a depth of between 20-1000 microns in a controlled and regulated manner. The plurality of heated tips may be embodied as an array of heated needles. This is described in greater detail below in FIG. 3A-3C. In general, in the case of using dermal conditioning device 200 on the eyelids, housing 212 may be placed up 3 millimeters from the eyelash line.

Figure 3A:
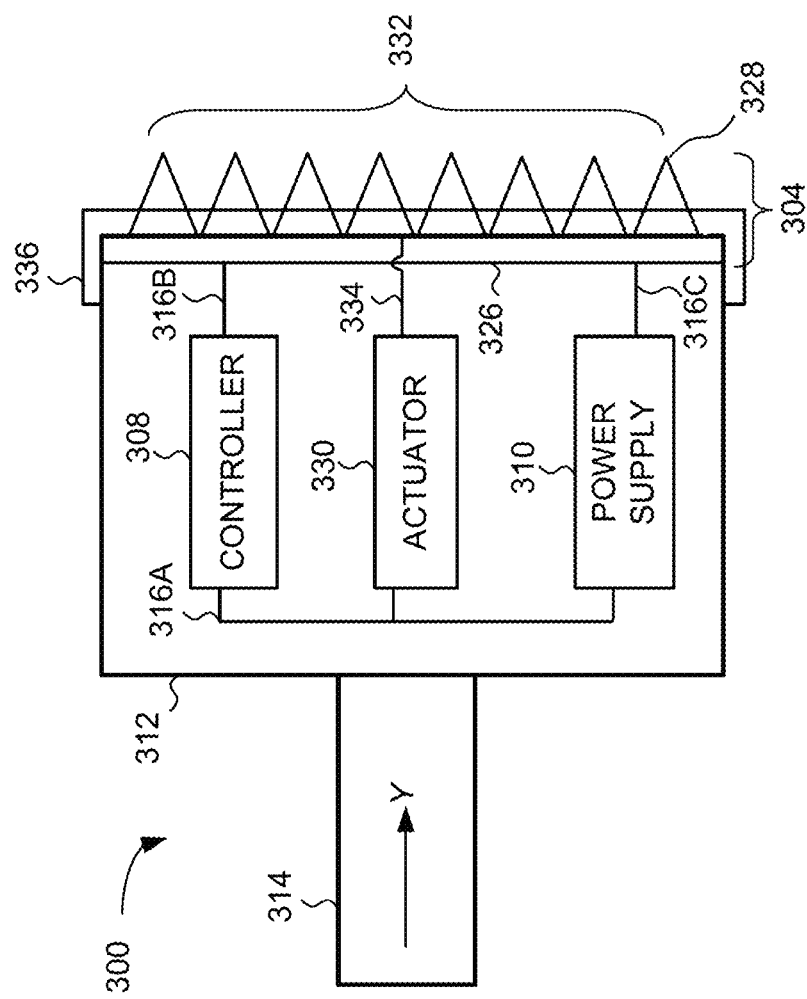
FIGS. 3A-3C, taken together, are a schematic illustration of an embodiment of the dermal conditioning device of the disclosed technique, constructed and operative in accordance with another embodiment of the disclosed technique.
Figure 3B:
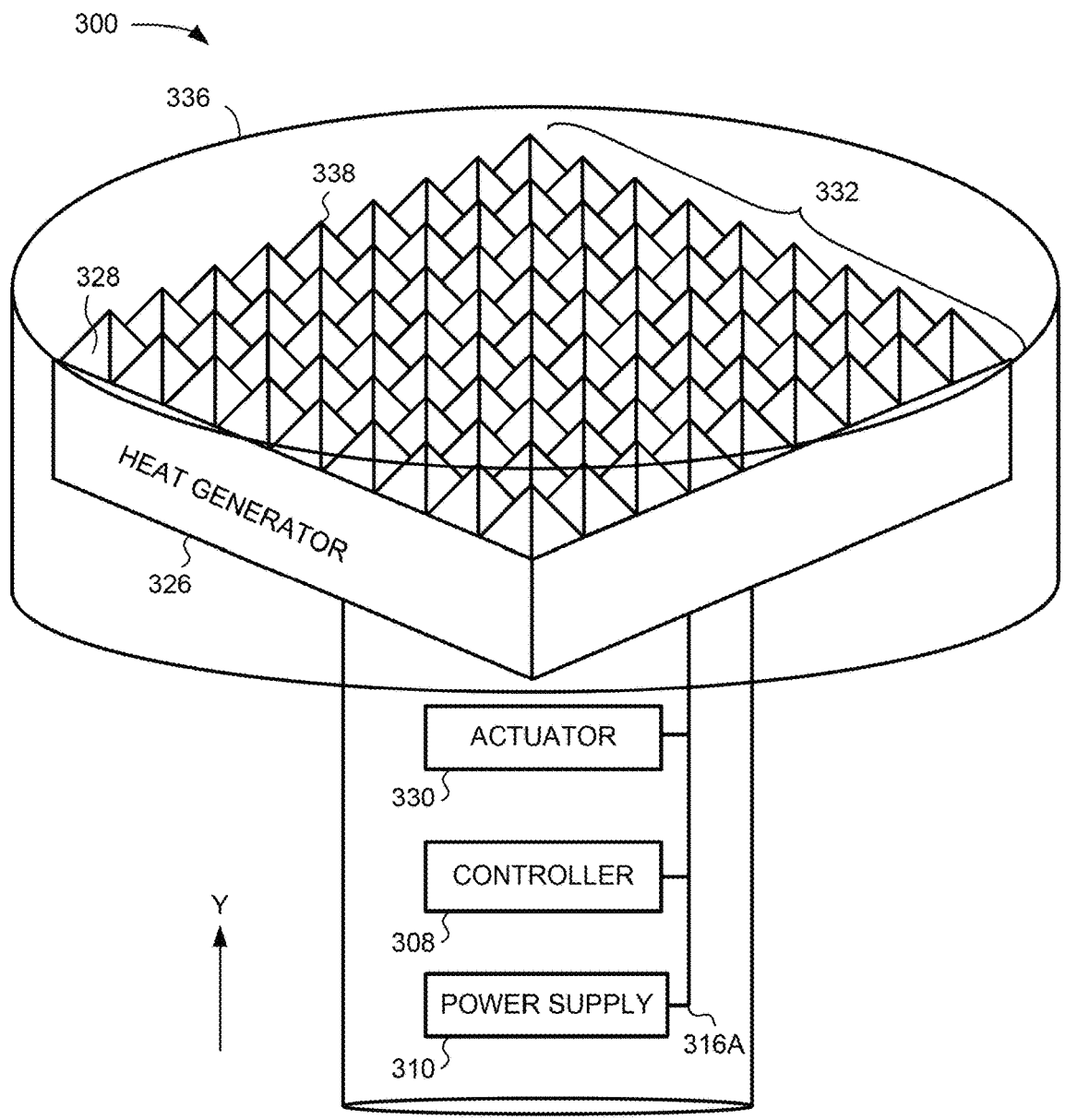
Figure 3C:
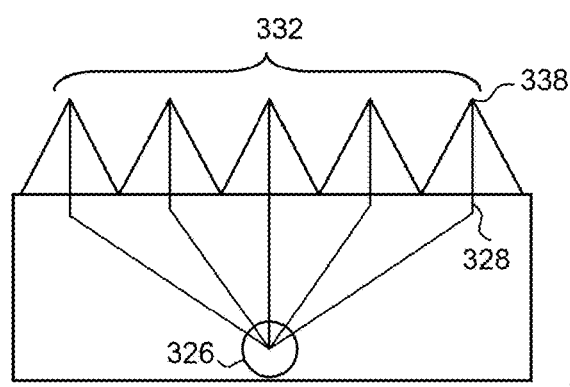

Reference is now made to FIGS. 3A-3C, which taken together, are a schematic illustration of an embodiment of the dermal conditioning device of the disclosed technique, generally referenced 300, constructed and operative in accordance with another embodiment of the disclosed technique. In the description that follows, dermal conditioning device 300 is understood to be operable to perform any of the procedures and/or functions described above with respect to dermal conditioning device 200 of FIGS. 2A-2C. With reference to FIG. 3A, dermal conditioning device 300 includes a controller 308, a power supply 310, communications buses 316A, 316B and 316C, respectively, a heater 304 comprising a heat generator 326, shown as a thin element at the distal end of housing 312 and a heat emitter 328, shown as a heat conducting surface of a set of pyramid-shaped teeth at the distal end of dermal conditioning device 300, an actuator 330, a shaft 334, an actuator tip 332 and a distance gauge 336. Referring back to FIGS. 2A-2B while still referring to FIG. 3A, controller 308 corresponds to controller 208, power supply 310 corresponds to power supply 210, heater 304, heat generator 326 and heat emitter 328 correspond to heater 204, heat generator 226 and heat emitter 228, respectively, and actuator 330 and actuator tip 332 correspond to actuator 230 and stress applier 232, respectively. Thus together, heater 304, heat generator 326, heat emitter 328, actuator 330 and actuator tip 332 can be considered an epidermal lesion generator.

Controller 308, actuator 330 and power supply 310 are electrically coupled via communications bus 316A. Controller 308 and power supply 310 are electrically coupled to heat generator 326 via communications buses 316B and 316C, respectively. Actuator 330 is mechanically coupled to actuator tip 332 via shaft 334. Actuator 330 is a linear motor operative to extend actuator tip 332 distally beyond distance gauge 336, and retract actuator tip 332 proximally behind distance gauge 336, in alignment with the longitudinal axis (Y) of dermal conditioning device 300, in accordance with the stress parameters. A more detailed description of actuator tip 332 is given below in FIG. 3B.

Heater 304 is positioned at the distal end of dermal conditioning device 300, proximal to actuator tip 332. Heater 304 may be embodied using any suitable technique known in the art. For example, heat generator 326 of heater 304 may be a thermal heater such as a ceramic heater. Alternatively, heat generator 326 of heater 304 may be a laser light source. Heater 304 provides constant heat to the distal end of dermal conditioning device 300. In one embodiment, heat emitter 328 is a thermally conductive coating on actuator tip 332 such that heat emitter 328, together with actuator tip 332, form the distal end of dermal conditioning device 300. In this embodiment, heat generator 326 of heater 304 is thermally coupled to heat emitter 328, such as by using a spring (not shown) that presses heat generator 326 against the proximal base of heat emitter 328 and actuator tip 332 to ensure thermal matching, or alternatively by using a thermally conductive adhesive. Controller 308 controls the operation of heat generator 326 of heater 304 to maintain heat emitter 328 at a constant, effective temperature of approximately 600° C. during operation of dermal conditioning device 300. In another embodiment of the disclosed technique, the temperature of heat emitter 328 is maintained at a constant, effective temperature of at least 37° C. during operation of dermal conditioning device 300. In the case of the eyelids, an effective temperature of at least 37° C. during operation will cause a sufficient burn to the eyelids to induce the body's natural healing process while nonetheless avoiding permanent damage and trauma to the eyelids. A higher temperature may induce tissue coagulation (without permanent damage or trauma to the eyelids and without damaging the eye itself) via the activation of thermal nociceptors in the eyelids. A higher temperature of heat emitter 328 may also enable actuator tips 332 to be in contact with the eyelids for less time in the embodiment of the disclosed technique where heat is also used. In general it is noted that actuator tips 332 transfer heat to the eyelids in a transient manner. According to the disclosed technique, the eyelids are dermally conditioned by a transient (i.e., time dependent) transfer of heat and not by a steady state heat transfer mechanism. This is achieved by the harmonic oscillating motion of the actuator tips which are advanced and then retracted, thus causing a transient transfer of heat. As mentioned above, the application of heat to the eyelids is optional and the disclosed technique primarily uses mechanical stress or force on the eyelids to induce the corneal, menace and lacrimation reflexes which do not require heat. The use of heat on the eyelids may enhance the treatment of DES and MGD by the disclosed technique.

With reference to FIG. 3B, dermal conditioning device 300 is shown from a perspective view. Actuator tip 332 is disposed at the distal end of dermal conditioning device 300. Actuator tip 332 includes an array of pyramid-shaped protrusions 338 that are aligned with the longitudinal axis of dermal conditioning device 300 (Y). In FIG. 3B, protrusions 338 are shown as pyramid-shaped protrusions having a square based. This is merely an example as protrusions 338 can have different geometries and shapes. For example, the base shape of protrusions 338 can be triangular, circular, oval as well as other known geometrical shapes. Protrusions 338 may also have a cone shape, a rod shape, a rectangular shape and the like. The apexes of array of protrusions 338 form the distal end of dermal conditioning device 300. As shown, the apexes of protrusions 338 are sharp. However in another embodiment of the disclosed technique, the apexes (i.e., the distal end) of protrusions 338 can be blunt, for example having a flat surface or a rounded surface, with each distal end of protrusions 338 covering an area of between 0.01-5 mm$^2$. In one embodiment, actuator tip 332 includes a 9×9 grid of array of protrusions 338 covering an area of approximately 1 cm$^2$. The height of each one of array of protrusions 338 is approximately 1.25 mm. The surface area of the distal end of each protrusion 338 (for example, the surface area making contact with stratum corneum layer 252 (FIG. 2A)) is approximately $1.27 \times 10^{-4}$ m$^2$. The spacing between the contact area of skin 250 and array of protrusions 338 of actuator tip 332 is sufficient, such that at any point in time, the temperature of any one of the contact areas of skin 250 with any one of array of protrusions 338 is thermally affected by only one of array of protrusions 338. Thus there are regions in between the areas of skin 250 in contact with array of protrusions 338 that remain at normal body temperature (i.e., 37° C.) throughout the treatment. Protrusions 338 may be made of a biocompatible, thermally conductive and thermally resilient material, such as gold-coated titanium, tungsten, tantalum or gold-coated stainless steel. In one embodiment of the disclosed technique, the thermal conductivity of protrusions 338 is less than the thermal conductivity of gold-coated copper to enable the heating of stratum corneum layer 252 (FIG. 2A) sufficiently to cause dehydration without causing ablation to viable tissue in area of skin 250 (FIG. 2A). Regarding the placement of array of protrusions 338, in the case of using dermal conditioning device 300 on the eyelids, the edge of array of protrusions 338 can be placed up to 3 mm from the eyelash line.

It is noted that all materials in dermal conditioning device 300 that comes in contact with a body (human or animal) need to be biocompatible. Since biocompatibility can depend on temperature (as certain materials lose their biocompatibility beyond a threshold temperature), the materials in the disclosed technique which come in contact with the body need to be such that they keep their biocompatibility within the temperature ranges that dermal conditioning device 300 may be used, for example between 37° C.-600° C. It is noted that dermal conditioning device 300 may use even higher temperatures in the case that heater 304 is embodied as a laser.

Distance gauge 336 of dermal conditioning device 300 is disposed at the respective distal end of dermal conditioning device 300. Distance gauge 336 encases array of protrusions 338 when dermal conditioning device 300 is not in use. During treatment, actuator 330 advances actuator tip 332 distally such that the distal end of protrusions 338 extend distally beyond distance gauge 336 by approximately 400 micrometers (herein abbreviated μm). In another embodiment of the disclosed technique, actuator 330 advances actuator tip 332 distally such that the distal end of protrusions 338 extend distally beyond distance gauge 336 by approximately 20-1000 μm. Actuator 330 is operative to advance and retract actuator tip 332 in a harmonic pulsating motion in accordance with a predefined pulse duration and a predefined number of pulses per treatment, as controlled by controller 308, causing frictional heat in addition to a stress on stratum corneum layer 252. For example, the harmonic pulsating motion may be 2-60 milliseconds in duration for fully advancing and retracting actuator tip 332. It is noted that in one embodiment of the disclosed technique, distance gauge 336 can be made from a transparent material, such that the eye can more easily perceive the advancing and retracting of actuator tip 332 (or any other element of dermal conditioning device 300 which moves) when actuator tip 332 is applied to the lower eyelids while the eye remains open. The increased perception of the eye regarding movement of actuator tip 332 may enhance the activation of the menace reflex (i.e., the hand-blink reflex) and the corneal reflex (i.e., the blink reflex) as the eye more easily perceives an object moving towards it. In another embodiment of the disclosed technique, housing 312 (FIG. 3A) is made from a transparent material to achieve the same effect.

During contact with area of skin 250 by plurality of protrusions 338, the distal ends of array of protrusions 338 depress the surface of skin 250 without penetrating stratum corneum layer 252 (FIG. 2A). Plurality of protrusions 338 depresses the surface of skin 250 in a non-invasive manner. The depression depth ranges between 0.1 millimeters (mm) to 1 mm, or from 0.05 to 1.2 mm, or from 0.2 mm to 0.8 mm, or from 0.3 mm to 0.7 mm, or from 0.4 to 0.6 mm or from 0.05 mm to 0.7 mm. Thus, the conditioning of skin 250 by dermal conditioning device 300 is non-invasive. The contact time between protrusions 338 and skin 250 varies between 1-20 milliseconds (herein abbreviated ms) to allow sufficient heat transfer between array of protrusions 338 and skin 250 to cause substantial dehydration of skin 250 without substantial coagulation or burning. Typical pulse durations may range from 8 ms to 14 ms, or from 5 ms to 20 ms, or from 10 ms to 15 ms, or from 5 ms to 15 ms or from 6 ms to 16 ms or from 2 ms to 60 ms. In one embodiment, the distance of the harmonic pulsating motion of actuator tip 332 may range between 0.02 mm to 1.50 mm along the longitudinal axis of dermal conditioning device 300. As mentioned above, the pulsating motion of actuator tip 332 may last for as short as a few seconds and as long as a few minutes during treatment. The combination of the pulsating motion of actuator tip 332 with the heating by heater 304 causes area of skin 250 to heat rapidly, resulting in the evaporation of water from the surface of skin 250 as well as the fissuring of stratum corneum layer 252. Additionally, once stratum corneum layer 252 has fissured, the continual application of heat by heater 304 evaporates water from deeper skin layers 254, 256 and 258 (FIG. 2A). It is noted that in one embodiment, distance gauge 336 may be replaced with a position sensor in housing 312 (as described above in FIGS. 2A and 2B), coupled with controller 308 and actuator 330, for precisely determining a distance which protrusions 338 extend into stratum corneum layer 252.

Reference is now made to FIG. 3C, which is a schematic illustration of another implementation for the distal end of dermal conditioning device 300 of FIG. 3A. Heater 304 (FIG. 3A) includes a heat generator 326, positioned proximal to actuator tip 332. Heat generator 326 can be an optical emitter, such as an intensed pulse light (herein abbreviated IPL) light source, an IR or near IR light source, a solid state laser diode and the like, and heat emitter 328 includes multiple optical channels embedded within plurality of protrusions 338 that direct the light from heat generator 326 to the distal end of dermal conditioning device 300. Heat generator 326 can thus generate heat by emitting radiation. Heat generator 326 may be implemented as a fractional $CO_2$ laser with a tissue penetration depth of 25 µm, 50 µm or 100 µm. Heat generator 326 may emit light at a wavelength of 2.94 µm, corresponding to the maximum absorption peak of water. Alternatively, the optical channels of heat emitter 328 may be positioned externally and adjacent to array of protrusions 338. Controller 308 (FIG. 3B) synchronizes the harmonic pulsating motion of actuator tip 332 with the emission of the light by heat generator 326. For example, controller 308 may control the emission of an IR laser by heat generator 326 such that the IR laser is emitted only when array of protrusions 338 makes physical contact with the area of skin 250. This may provide a safety measure to prevent the emission of the IR laser unless the device is in physical contact with the surface of area of skin 250. Alternatively, a sensor (not shown) may sense contact between actuator tip 332 and area of skin 250 and notify controller 308 to activate heat generator 326. The sensor may similarly notify controller 308 to deactivate heat generator 326 when no contact is detected between actuator tip 332 and area of skin 250. Heat generator 326 may also be embodied as a non-radiation emitting heating device and may transfer heat via convection or conduction.

Figure 3D:
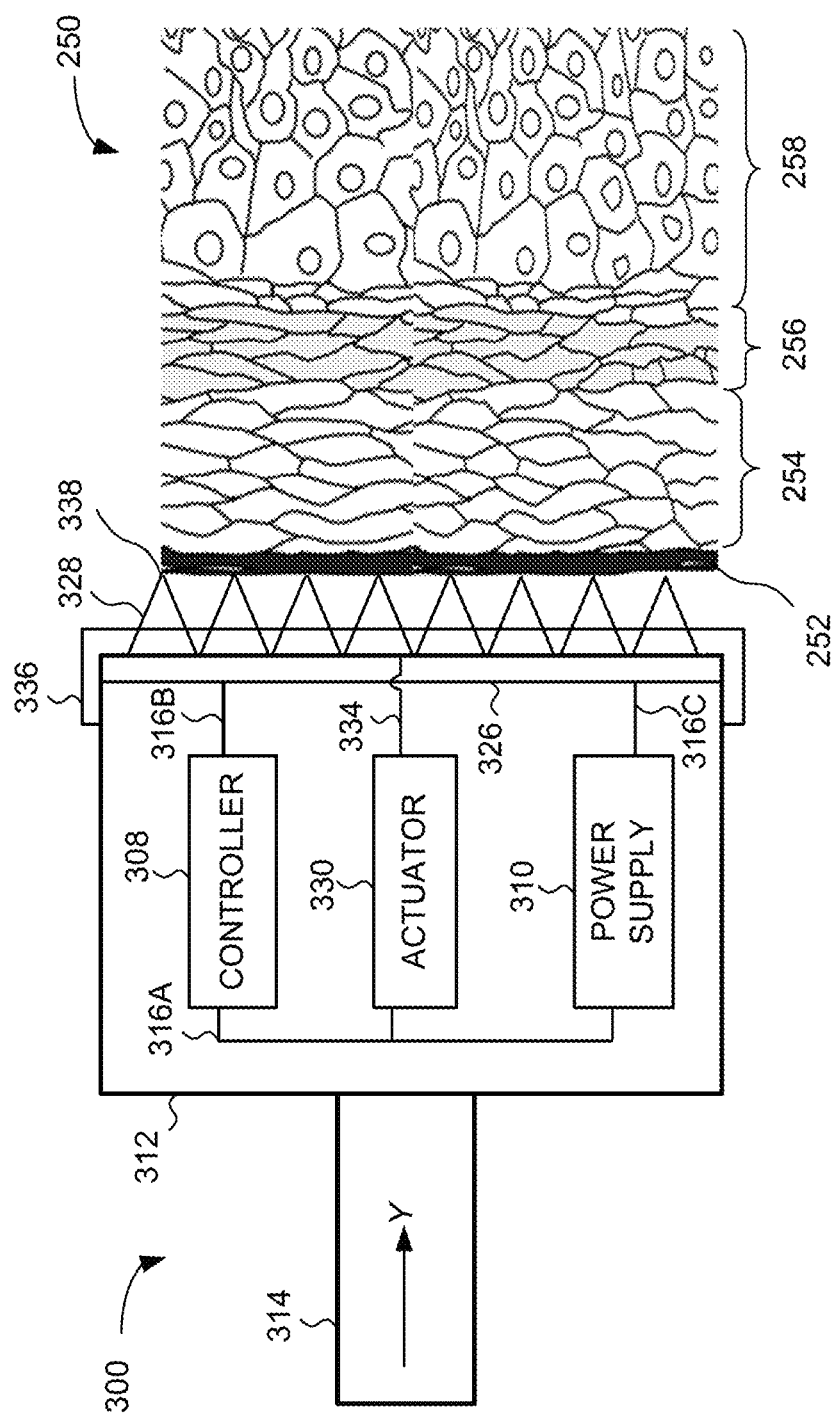
FIGS. 3D-3E are schematic illustrations of a sample of eyelid skin undergoing a mechanical lesion treatment by the dermal conditioning device of FIGS. 3A-3C, constructed and operative in accordance with a further embodiment of the disclosed technique.
Figure 3E:
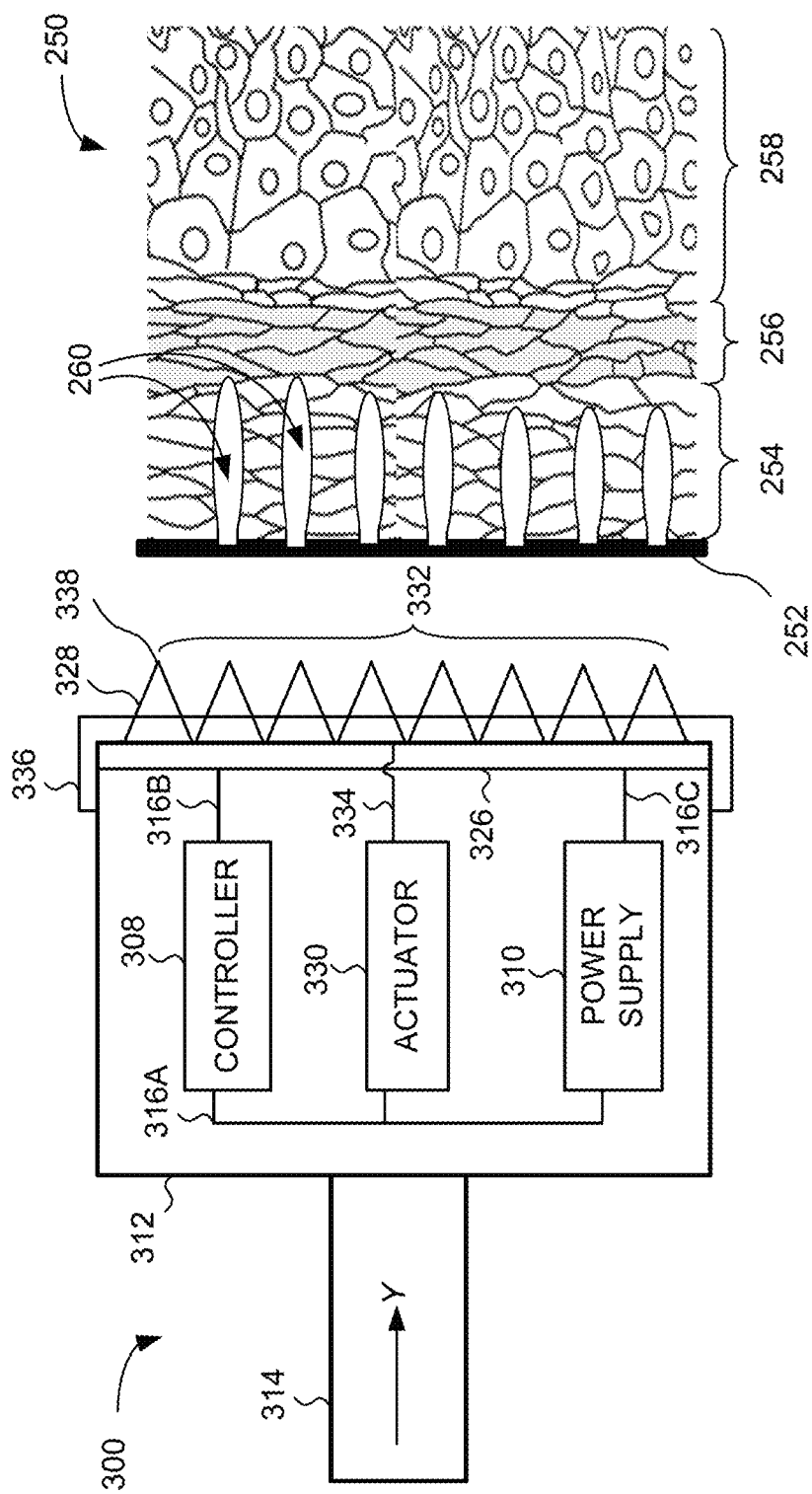

Reference is now made to FIGS. 3D-3E, which are schematic illustrations of a sample of eyelid skin undergoing a mechanical lesion treatment by the dermal conditioning device of FIGS. 3A-3C, generally referenced 300, constructed and operative in accordance with a further embodiment of the disclosed technique. FIG. 3D shows an area of skin 250 prior to conditioning by a dermal conditioning device 300 and FIG. 3E shows area of skin 250 after conditioning by dermal conditioning device 300. With reference to FIG. 3D, the surface temperature of skin 250 is 37° C. (normal skin temperature) and skin 250 is fully hydrated. Stratum corneum layer 252 is intact serving as a barrier between the external surface of skin 250 and deeper skin layers 254, 256 and 258. With reference to FIG. 3E, skin 250 is lesioned. Stratum corneum layer 252 and deeper skin layer 254 present a plurality of lesions 260 that function to activate the corneal, menace and lacrimation reflexes of the eye and to optionally induce the inflammatory healing process of the body.

In one embodiment, to achieve this conditioning of area of skin 250, controller 308 controls heat generator 326 to raise the temperature of the distal end of dermal conditioning device 300 up to 600° C. The temperature may also be raised at minimum 37° C. A higher temperature of the distal end of dermal conditioning device 300 may enable a reduction in contact time between the distal end and skin 250. Controller 308 sends a control signal to actuator 330 driving actuator tip 332 at pulses ranging from 2 ms to 60 ms. This range of pulses is brought merely as an example and the pulse range may vary from 2 ms to 60 ms. According to the disclosed technique, the duration of the stress pulses and the surface temperature of the distal end of dermal conditioning device 300 are computed in accordance with the following equation between the thermal wave penetration depth and the thermal properties of area of skin 250, analyzed using the lumped system analysis given above in equations (6)-(9):

$$\delta = 3.6\sqrt{\alpha t} = 3.6\sqrt{\frac{k}{\rho C_p}t} \qquad (10)$$

where δ is the thermal wave penetration depth in meters, α is the thermal diffusivity in units of m²/s, t is the time in seconds, k is the heat conductivity in units of W/m·° K, ρ is the density in units of Kg/m$^3$ and $C_p$ is the heat capacity at constant pressure in units of J/(Kg·° K).

Table 1 below gives heat conducting properties for area of skin 250.

TABLE 1

Heat conductivity respective of tissue density and heat capacity for different layers of area of skin 250

| | Conductivity (k) (W/m · ° K) | Density (ρ) (Kg/m$^3$) | Heat Capacity ($C_p$) (J/Kg · ° K) |
|---|---|---|---|
| epidermis | 0.24 | 1200 | 3590 |
| dermis | 0.45 | 1200 | 3300 |
| fat | 0.45 | 900 | 3300 |

Heat transfer from actuator tip 332 to area of skin 250 may be calculated according to the following equations:

$$Heat_{flux} = \int\int (\text{total heat flux})\, dA \quad (11)$$

Equation (11) describes the heat flux for each of array of protrusions 338 respective of area of skin 250. As per equation (11), the heat flux is calculated by integrating the heat flux per protrusion 338 over the contact surface area, A, of each of protrusions 338 with the surface skin 250. Thus the total amount of energy transferred to the area of skin 250 can be expressed by the following equation:

$$Total_Q = \int_0^t (Heat_{flux})\, dt \quad (12)$$

This equation describes the amount of energy transferred to skin 250 from each of protrusions 338 for each pulse of duration t, and which is calculated by integrating the $Heat_{flux}$ per protrusion 338, calculated above in equation (11), over pulse duration t.

$$Q_{total_{tip}} = n * Total_Q \quad (13)$$

This equation describes the amount of energy transferred to skin 250 from actuator tip 332 per pulse, calculated by multiplying the amount of energy transferred per protrusion 338 per pulse, by the number n of protrusions 338, which in the embodiment shown in FIG. 3B is 81. Plurality of protrusions 338 may be arranged according to need. For example, plurality of protrusions 338 may be arranged as a 4×6 array, a 12×12 array, a 10×10 array, a 15×15 array, a 10×15 array and the like.

Table 2 below shows the amount of heat transferred from actuator tip 332 to skin 250 and the thermal penetration depth for a pulse duration of 8 ms and a pulse duration of 14 ms, respectively, as determined from a finite element analysis of dermal conditioning device 300 as described above in equations (6)-(9):

TABLE 2

Amount of heat transfer (J) to skin 250 by actuator tip 332 and thermal penetration depth (μm) of the applied heat for varying pulse durations (8 ms and 14 ms)

| Pulse Duration (ms) | Heat Transfer (J) | Thermal Penetration (μm) |
|---|---|---|
| 8 | 0.024 | 76 |
| 14 | 0.035 | 100 |

As mentioned above, plurality of lesions 260 may also be formed by merely advancing and retracting protrusions 338 into stratum corneum layer 252 to a predetermined depth using sufficient mechanical stress and force without the application of heat.

Figure 4A:
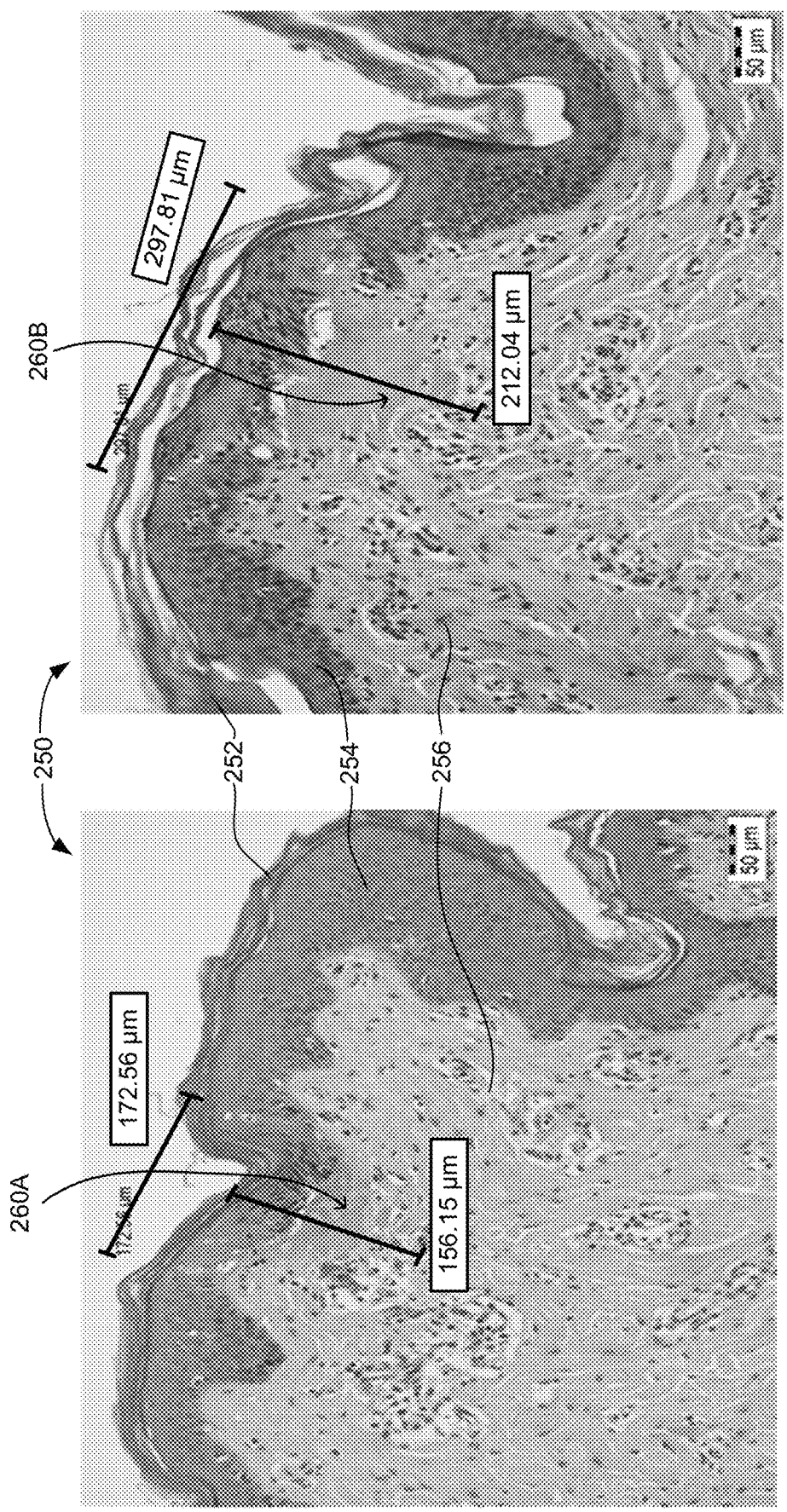
FIG. 4A shows two images of an area of skin after undergoing the mechanical lesion treatment by the dermal conditioning device of FIGS. 3A-3C, constructed and operative in accordance with another embodiment of the disclosed technique.

Reference is now made to FIGS. 4A-4D, which illustrate the response of skin 250 to treatment by dermal conditioning device 300 of FIGS. 3A-3E at pulse durations of 8 ms and 14 ms using the embodiment of the disclosed technique wherein heat is applied. The numerical results were obtained from a finite element analysis of the skin, using equations (6)-(9) as given above. With reference to FIG. 4A, two images of an area of skin are shown after undergoing the mechanical lesion treatment by the dermal conditioning device of FIGS. 3A-3E, generally referenced 250, constructed and operative in accordance with another embodiment of the disclosed technique. It is noted that the images shown in FIG. 4A are merely brought as examples and that the examples shown are from pig skin. Skin 250 is shown having a lesion extending through stratum corneum layer 252, stratum granulosum layer 254 and partially into stratum spinosum layer 256. As shown, a lesion 260A has a width of 172.56 μm and a depth of 156.15 μm and a lesion 260B has a width of 297.81 μm and a depth of 212.04 μm. The widths and depths of lesions 260A and 260B are merely brought as examples, and deeper and wider lesions are possible according to the disclosed technique, for example between 20-1000 μm in depth and up to 700 μm in width. Skin 250 was mechanically perforated by protrusions 338 (FIG. 3B). Skin 250 could also be created by the combination of the dehydration and the non-invasive compression load/stress applied to stratum corneum layer 252 by dermal conditioning device 300 (FIGS. 3A-3E), and the resulting strain on stratum corneum layer 252 caused by this stress.

It is noted as well that the thermal model for determining the parameters of the heater for generating mechanical lesions in the skin tissue as presented above may yield different results as compared to the actual lesion depths and widths as shown in FIG. 4A (and also below in FIG. 6C). Variations in the thermal properties used in the model can account for these differences. Thus according to the disclosed technique, when using the thermal model presented above to determine the parameters of the heater for generating lesions in the skin tissue of the eyelids, the thermal properties of the skin tissue of the eyelids along with the thermal properties of the actual materials used in the dermal conditioning device of the disclosed technique need to be taken into account and tweaked appropriately.

Figure 4B:
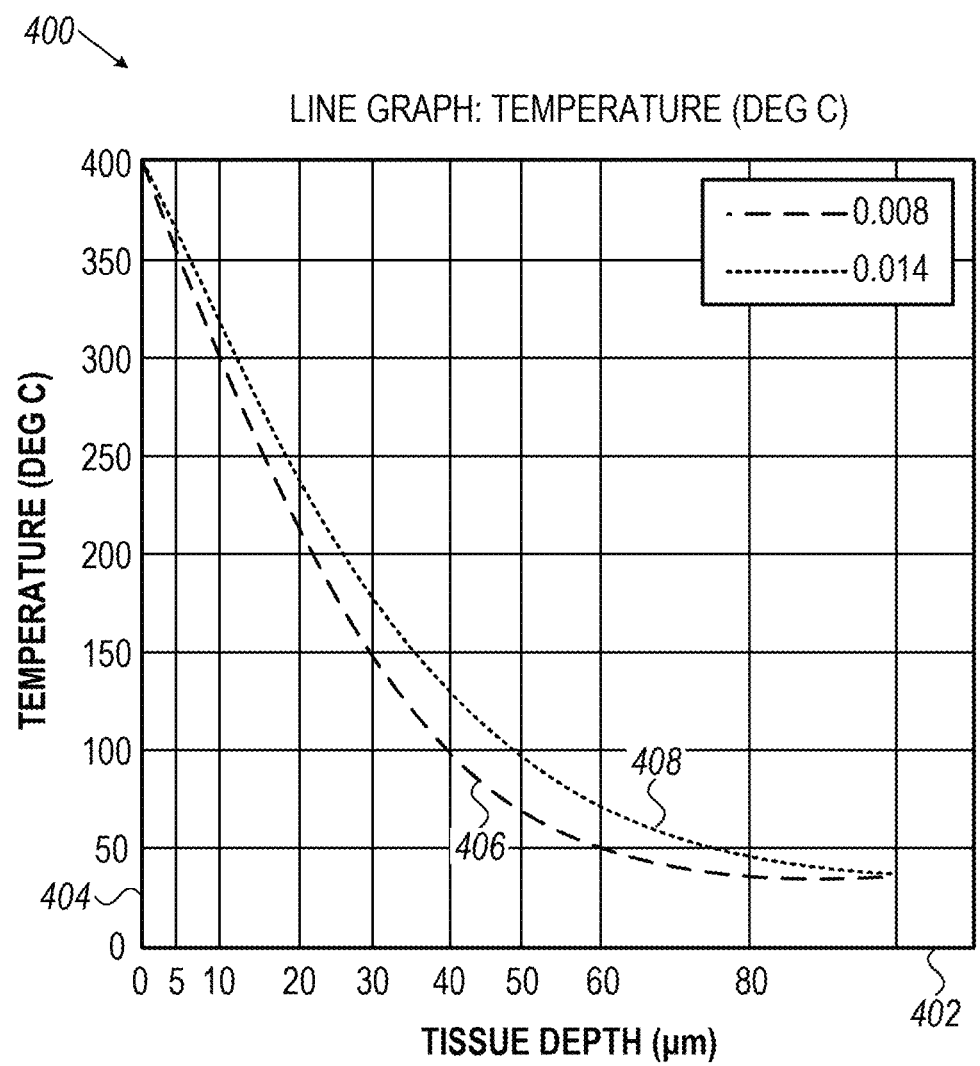
FIG. 4B is a graph illustrating the heat wave penetration depth for skin responsive to treatment by the dermal conditioning device of FIGS. 3A-3C, constructed and operative in accordance with a further embodiment of the disclosed technique.

With reference to FIG. 4B, a graph illustrating the heat wave penetration depth for skin responsive to treatment by dermal conditioning device of FIGS. 3A-3C is shown, generally referenced 400, constructed and operative in accordance with a further embodiment of the disclosed technique. Graph 400 includes a horizontal axis 402 showing tissue depth in micrometers and a vertical axis 404 showing temperature in degrees Celsius. A curve 406 depicts the heat wave penetration depth for skin 250 responsive to being treated by dermal conditioning device 300 (FIGS. 3A-3C) with a pulse duration of 8 ms whereas and a curve 408 depicts the heat wave penetration depth for skin 250 responsive to being treated by dermal conditioning device 300 with a pulse duration of 14 ms. With respect to curve 406 respective of an 8 ms pulse duration, at a depth of 0 µm, the temperature of skin 250 reaches 400° C., at a depth of 5 µm the temperature of skin 250 reaches 350° C., at a depth of 10 µm the temperature of skin 250 reaches 300° C., and at a depth of 30 µm the temperature of skin 250 reaches 150° C. With respect to curve 408 respective of a 14 ms pulse duration, at a depth of 0 µm, the temperature of skin 250 reaches 400° C., at a depth of 5 µm the temperature of skin 250 reaches 360° C., at a depth of 10 µm the temperature of skin 250 reaches 320° C. and at a depth of 30 µm the temperature of skin 250 reaches 180° C. As can be seen from curves 406 and 408, the most significant temperature increase occurs at the surface of skin 250, at a depth of 0 µm. The temperature of the deeper layers of skin 250, e.g. layers 254, 256 and 258 of FIGS. 3D-3E, decreases dramatically at a steep slope, tapering at about 50 µm, where the temperature decreases at a gentle slope. This characteristic prevents ablation and tissue damage at the deeper skin layers, maintaining the viability of these cells.

Figure 4C:
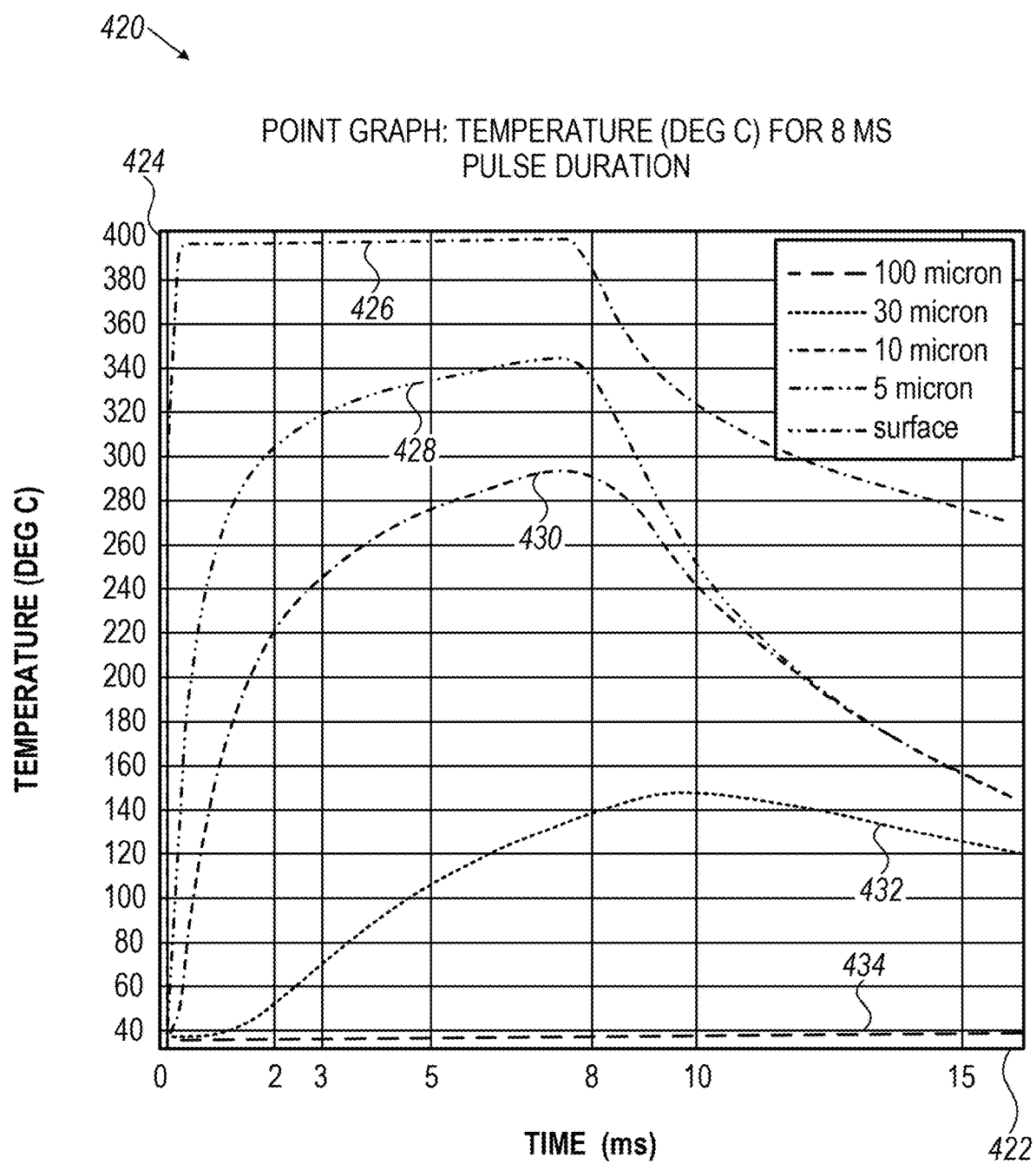
FIG. 4C is a graph showing the temperature of skin at varying skin depths over 15 ms after treatment by the dermal conditioning device of FIGS. 3A-3C for a pulse duration of 8 milliseconds, constructed and operative in accordance with another embodiment of the disclosed technique.

Reference is now made to FIG. 4C, which is a graph showing the temperature of skin at varying skin depths over 15 ms after treatment by the dermal conditioning device of FIGS. 3A-3C for a pulse of duration 8 ms, generally referenced 420, constructed and operative in accordance with another embodiment of the disclosed technique. Graph 420 includes a horizontal-axis 422 showing time in milliseconds and a vertical-axis 424 showing temperature in degrees Celsius. The topmost curve, referenced 426, illustrates the changes to the surface temperature of skin 250, in other words the external side of stratum corneum layer 252, over 15 ms on being treated to an 8 ms pulse by device 300. At the onset of the pulse, the surface temperature of skin 250 rises rapidly, reaching the peak temperature of 400° C. within 1 ms. The surface of stratum corneum layer 252 is maintained at a constant temperature of 400° C. for the 8 ms duration of the pulse, after which the temperature begins to drop, reaching 320° C. after 10 ms and approximately 260° C. after 15 ms.

The curve referenced 428 illustrates the changes to the temperature of skin 250 over 15 ms at a depth of 5 µm, corresponding to the middle region of stratum corneum layer 252, on being treated to an 8 ms pulse by dermal conditioning device 300. At the onset of the pulse, the temperature increases rapidly for the first 2 ms, reaching approximately 300° C., after which the temperature continues to increase at a slower rate, reaching a peak temperature of nearly 350° C. at 8 ms. After 8 ms, the temperature decreases fairly rapidly, falling to about 250° C. at 10 ms and continuing to decrease below 160° C. after 15 ms.

The curve referenced 430 illustrates the changes to the temperature of skin 250 over 15 ms at a depth of 10 µm, corresponding to the border between stratum corneum layer 252 and stratum granulosum 254, on being treated to an 8 ms pulse by dermal conditioning device 300. At the onset of the pulse, the temperature increases rapidly for the first 3 ms, reaching 260° C., after which the temperature continues to increase at a slower rate, reaching a peak temperature of nearly 300° C. at 8 ms. After 8 ms, the temperature decreases fairly rapidly, falling to about 240° C. at 10 ms and continuing to decrease below 160° C. after 15 ms. Curves 430 (10 µm) and 428 (5 µm) converge after about 12 ms. The curve referenced 432 illustrates the changes to the temperature of skin 250 over 15 ms at a depth of 30 µm, corresponding to just below stratum basale 258 (the border between the epidermis and dermis layers of the skin), on being treated to an 8 ms pulse by dermal conditioning device 300. At the onset of the pulse, the temperature increases almost linearly, reaching almost 150° C. after 8 ms. After 8 ms, the temperature decreases fairly linearly, but slower than the increase, reaching 120° C. after 15 ms.

The curve referenced 434 illustrates the changes to the temperature of tissue beneath skin 250 over 15 ms at a depth of 100 µm, on being treated to an 8 ms pulse by dermal conditioning device 300. At the onset of the pulse, the temperature of the deep tissue barely changes from normal body temperature of 37° C., reaching 40° C. after 15 ms.

As may be seen from graph 420, only the surface temperature of skin 250, represented by curve 426, is maintained at 400° C. throughout the duration of the pulse, allowing for significant dehydration and the formation of fissures. The temperature of the deeper skin layers 254 and 256, at depths of 5 µm and 10 µm respectively, represented by curves 428 and 430, rises somewhat allowing for dehydration without causing damage to the viable cells. However the temperature of the deep tissue, beneath 30 µm until 100 µm, represented by curves 432 and 434, respectively, rises only mildly, preventing damage to these areas.

Figure 4D:
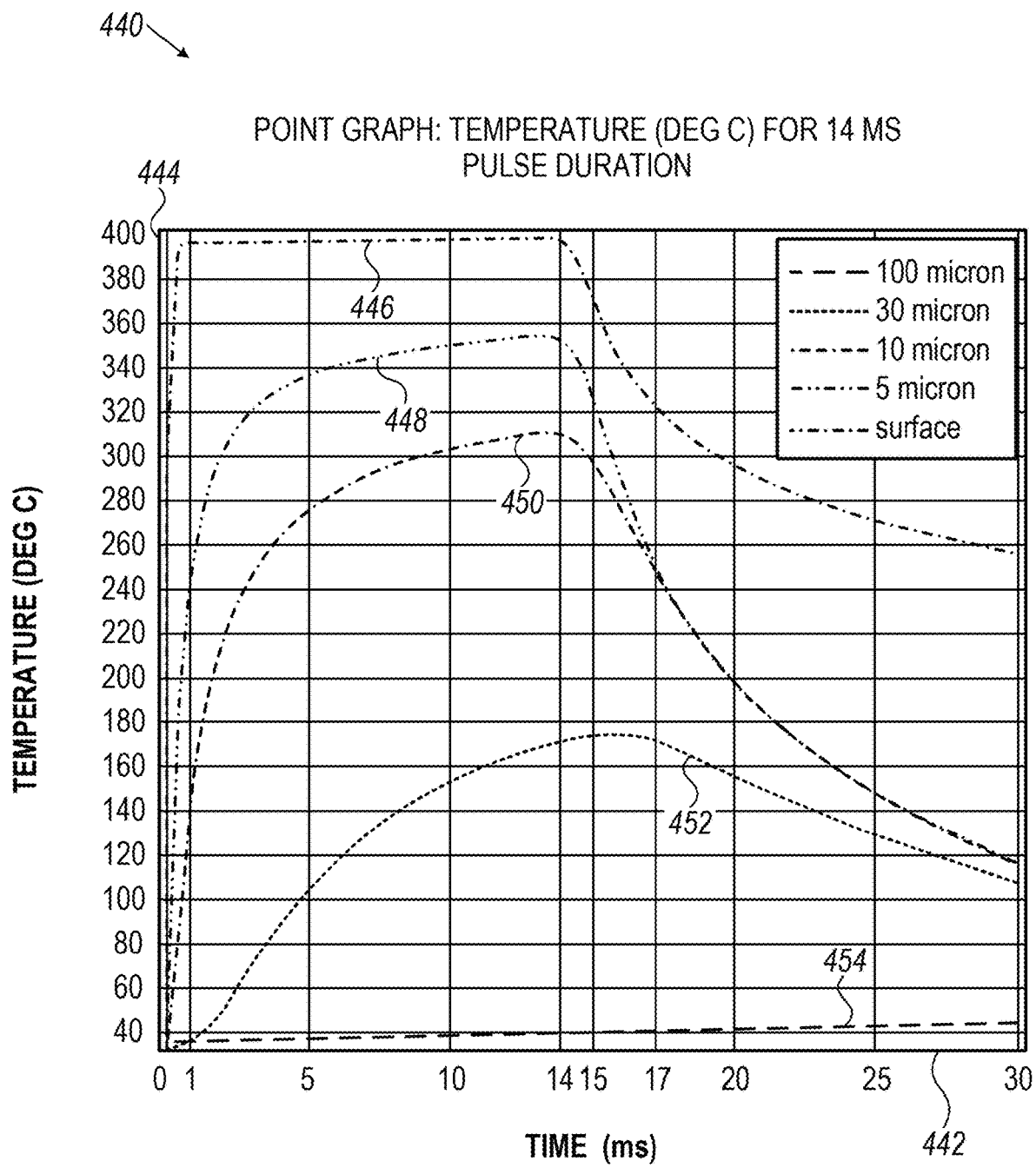
FIG. 4D is a graph showing the temperature of skin at varying skin depths over 30 ms after treatment by the dermal conditioning device of FIGS. 3A-3C for a pulse duration of 14 milliseconds, constructed and operative in accordance with a further embodiment of the disclosed technique.

Reference is now made to FIG. 4D which is a graph showing the temperature of skin at varying skin depths over 30 ms after treatment by the dermal conditioning device of FIGS. 3A-3C for a pulse of duration 14 ms, generally referenced 440, constructed and operative in accordance with a further embodiment of the disclosed technique. Graph 440 includes a horizontal-axis 442 showing time in milliseconds and a vertical-axis 444 showing temperature in degrees Celsius. The topmost curve, referenced 446 illustrates the changes to the surface temperature of skin 250, i.e. the external side of stratum corneum layer 252, over 30 ms on being treated to a 14 ms pulse by dermal conditioning device 300 (FIGS. 3A-3C). At the onset of the pulse, the surface temperature of skin 250 rises rapidly, reaching the peak temperature of 400° C. within 1 ms. The surface of stratum corneum layer 252 is maintained at a constant temperature of 400° C. for the 14 ms duration of the pulse, after which the temperature begins to drop, reaching 370° C. after 15 ms and just below 260° C. after 30 ms.

The curve referenced 448 illustrates the changes to the temperature of skin 250 over 30 ms at a depth of 5 µm, corresponding to the middle region of stratum corneum layer 252, on being treated to a 14 ms pulse by dermal conditioning device 300. At the onset of the pulse, the temperature increases rapidly for the first 3 ms, reaching approximately 320° C., after which the temperature continues to increase at a slower rate, reaching a peak temperature of nearly 360° C. at 14 ms. After 14 ms, the temperature decreases fairly rapidly, falling to about 240° C. at 17 ms, and continuing to decrease to below 120° C. after 30 ms.

The curve referenced 450 illustrates the changes to the temperature of skin 250 over 30 ms at a depth of 10 µm, corresponding to the border between stratum corneum layer 252 and stratum granulosum 254, on being treated to a 14 ms pulse by dermal conditioning device 300. At the onset of the pulse, the temperature increases rapidly for the first 3 ms, reaching 260° C., after which the temperature continues to increase at a slower rate, reaching a peak temperature of approximately 310° C. at 17 ms. After 14 ms, the temperature decreases fairly rapidly, falling to about 240° C. at 17 ms, and continuing to decrease below 120° C. after 30 ms. The 10 µm curve 450 and the 5 µm curve 448 converge after about 17 ms.

The curve referenced 452 illustrates the changes to the temperature of skin 250 over 30 ms at a depth of 30 µm, corresponding to just below stratum basale 258, on being treated to a 14 ms pulse by dermal conditioning device 300. At the onset of the pulse, the temperature increases more gradually throughout the duration of the pulse, reaching a peak temperature of nearly 180° C. at 14 ms, after which the temperature decreases gradually, falling to just below 110° C. at 30 ms.

The curve referenced 454 illustrates the changes to the temperature of tissue beneath skin 250 over 30 ms at a depth of 100 µm, on being treated to a 14 ms pulse by dermal conditioning device 300. At the onset of the pulse, the temperature of the deep tissue barely changes from normal body temperature of 37° C., reaching just under 45° C. after 30 ms.

As may be seen from graph 440, the temperature rise and decay patterns are similar as for graph 420 (FIG. 4C). Only the surface temperature of skin 250, represented by curve 446, is maintained at 400° C. throughout the duration of the pulse, allowing for significant dehydration and the formation of fissures on the stratum corneum. The temperature of the deeper skin layers 254 and 256, at depths of 5 µm and 10 µm respectively, represented by curves 448 and 450, rises somewhat allowing for partial dehydration without causing damage to the viable cells therein. However the temperature of the deep tissue, beneath 30 µm until 100 µm, represented by curves 452 and 454, respectively, rises only mildly, thereby preventing damage to these areas.

In general, the application of the heating stage by dermal condition device 300 (FIG. 3A), and more generally by dermal condition device 200 (FIG. 2A) on skin 250, causes the dehydration of stratum corneum layer 252 and deeper skin layers 254, 256 and 258. As a result of the dehydration, there is a concentration gradient between a solution, subsequently introduced to the external surface of skin 250, and dehydrated stratum corneum layer 252 and deeper skin layers 254, 256 and 258. The concentration gradient is greater than any concentration gradient present in other areas of skin 250 that were not treated by dermal conditioning device 200. The concentration gradient caused by the conditioning of skin 250 by dermal conditioning device 200 aids in accelerating the absorption of the introduced solution through stratum corneum layer 252, into the viable cells residing in deeper skin layers 254, 256 and 258. Additionally, when stratum corneum layer 252 is dehydrated, the concentration gradient external to stratum corneum layer 252 of the skin is substantial. For example the solution may have a water content ranging between 75% and 100%, or between 80% and 90%, or between 60% and 100%, and the water content of dehydrated stratum corneum layer 252 may range between 0% and 10%, or between 5% and 15%, or between 10% and 20%. By contrast, the concentration gradient internal to stratum corneum layer 252 is less substantial. For example, stratum granulosum layer 254 may be dehydrated to reach a water content of 70%, or 75%, or 65%, or 80%, corresponding to the heat penetration depth. The water content level of stratum granulosum layer 254 gradually decreases from this level as the distance from dehydrated stratum corneum layer 252 decreases, i.e. moving upwards through partially dehydrated stratum granulosum layer 254, transitioning through water content levels 50%, 40%, 30% and 20% to reach dehydrated stratum corneum layer 252 having a water content ranging from 0% to 10%, or from 5% to 15%. This difference between the concentration gradient external to skin 250 versus the concentration gradient internal to skin 250 may further accelerate the absorption of an externally applied solution.

Additionally, the total amount of heat energy applied to skin 250 by dermal condition device 300 (FIG. 3A), and more generally by dermal condition device 200 (FIG. 2A), during treatment is relatively small. The applied heat energy is a function of the physical dimensions and design of dermal conditioning device 200 in general. A heat transfer analysis describing the applied heat energy for the specific case of dermal condition device 300 (FIG. 3A) is described above in equations 11-13. The heat transfer analysis takes into account the size, shape and material of actuator tip 332, and additionally of the method by which controller 308 controls the application of heat by heat emitter 328 in accordance with the heat parameters (e.g. pulses of 8 ms and 14 ms, heating actuator tip to 400° C., etc). However, such analysis is not intended to be limited to the embodiment of FIGS. 3A-3E. It is to be understood that a similar heat transfer analysis may be performed for each of the embodiments disclosed herein, in accordance with heat transfer analysis as is known in the art, to achieve the desired heat energy transfer to skin 250 that fissures stratum corneum layer 252 without causing excess coagulation.

Figure 1B:
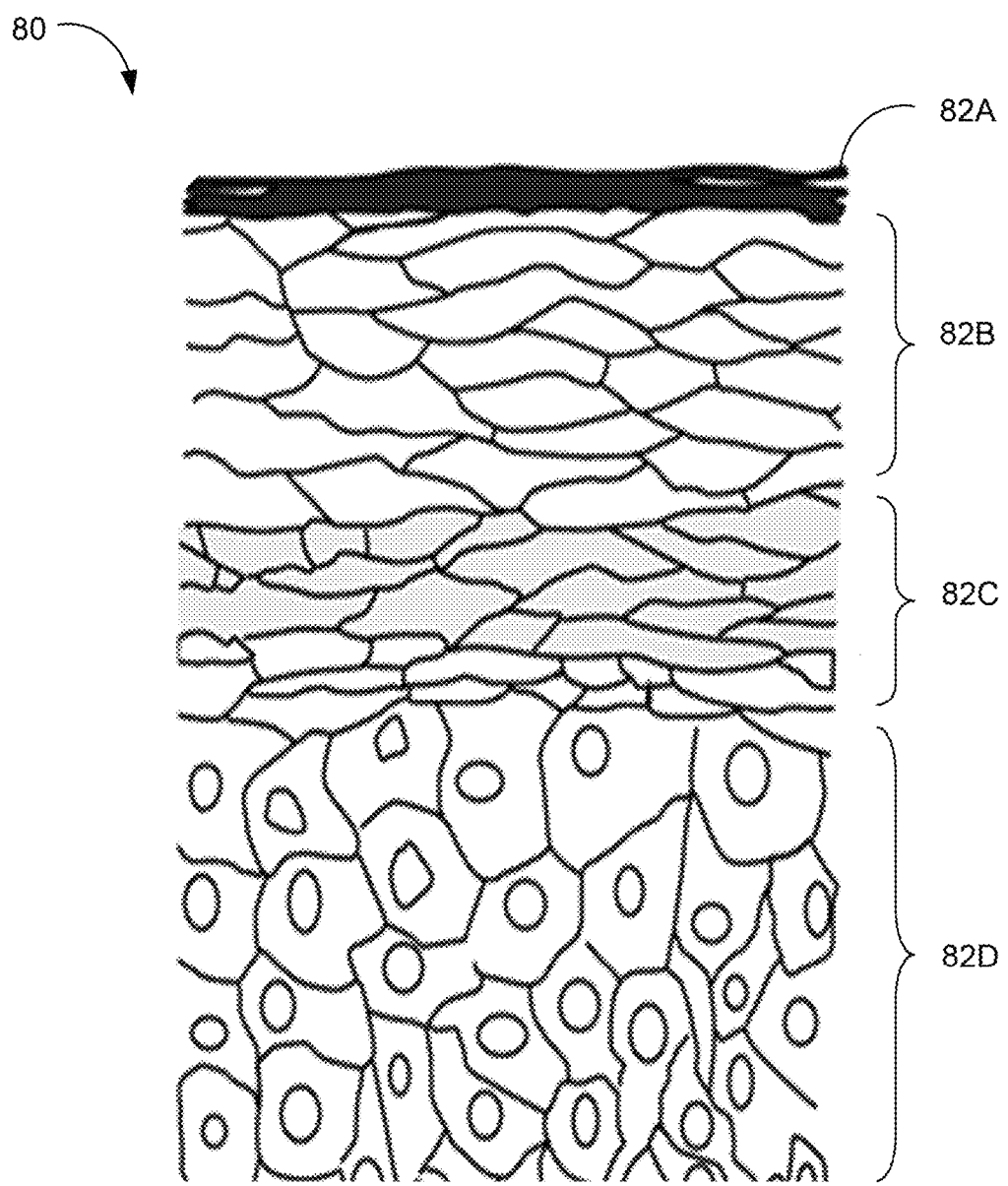
FIG. 1B is a schematic illustration of a cross section of a sample of epidermis, as is known in the prior art.

Accordingly, the amount of coagulated tissue within skin 250 on being treated by dermal conditioning device 300 (FIG. 3A), and in general by dermal conditioning device 200 (FIG. 2A), is significantly reduced as compared to conventional techniques. This reduction in skin coagulation is evident by comparing skin 80 (FIG. 1B), having been treated by prior art techniques with skin 250 (FIG. 4A), having been treated by dermal condition device 300 (FIG. 3A), and more generally by dermal condition device 200 (FIG. 2A). As may be seen by comparing these images, the coagulation present in skin 80 (FIG. 1B) is significantly greater than any coagulation present in skin 250 (FIG. 4A). This reduction in tissue coagulation reduces the barrier posed by such tissue coagulation, further enhancing the absorption capability by the viable cells of deeper skin layers 254, 256 and 258, to the introduced solution.

Figure 4E:
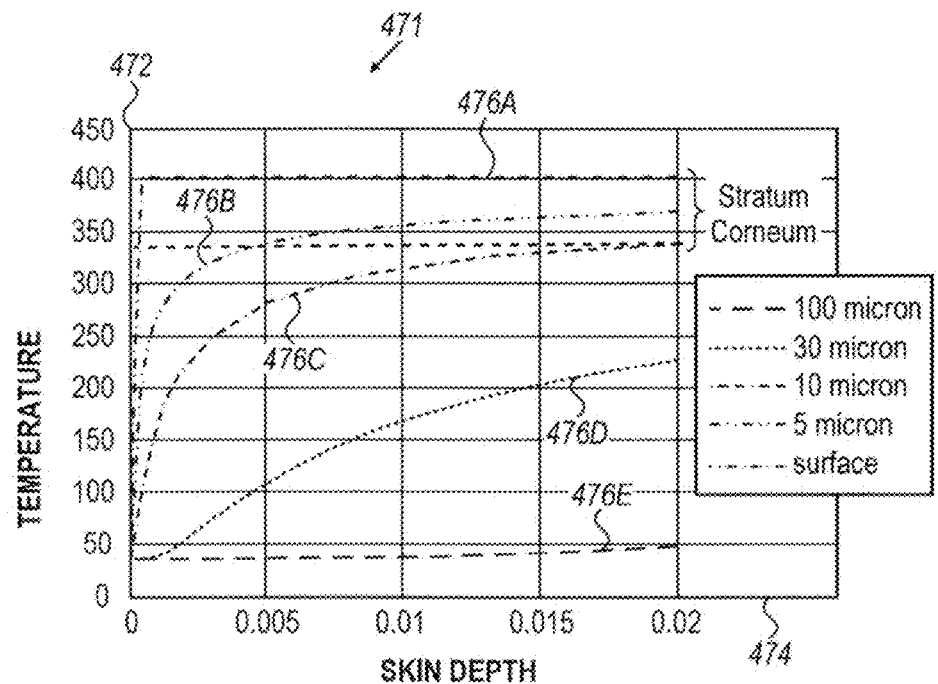
FIG. 4E is a graph showing the temperature of the skin at a plurality of depths, in response to the application of the heating stage of the dermal conditioning device of FIG. 2A in general, and the dermal conditioning device of FIG. 3A, in particular, constructed and operative in accordance with a further embodiment of the disclosed technique.

Reference is now made to FIG. 4E which is a graph, generally referenced 471, showing the temperature of the skin at a plurality of depths, in response to the application of the heating stage by any of dermal conditioning device 200 (FIG. 2A) in general and dermal conditioning device 300 (FIG. 3A) in particular, constructed and operative in accordance with a further embodiment of the disclosed technique. The applied heat is indicated on the vertical axis 472, labeled "Temperature" as measured in ° C., and the skin depth is indicated on the horizontal axis 474, labeled "skin depth" as measured in µm. Curve 476A shows the temperature of skin 250 at the surface corresponding to a depth of 0 microns (µm), curve 476B shows the temperature of skin 250 at a depth of 5 µm and curve 476C shows the temperature of skin 250 at a depth of 10 µm. Curves 476A, 476B and 476C relate to stratum corneum layer 252. Accordingly, the temperature of stratum corneum layer 252 increases dramatically in response to the heating stage and is maintained at a high temperature, ranging from 400° C. to 340° C. Curve 476D shows the temperature of skin 250 at a depth of 30 µm. At this depth, the temperature of the skin rises far more gradually and does not exceed 250° C. Curve 476E shows the temperature of skin 250 at a depth of 100 µm. At this depth, the temperature of the skin barely rises, reaching 50° C.

Figure 4F:
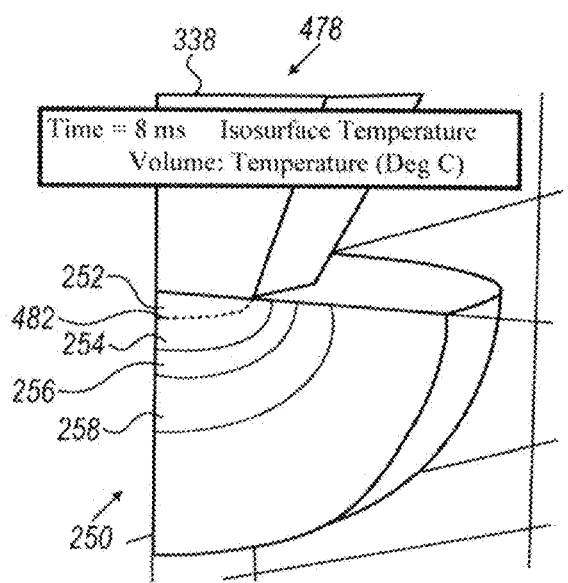
FIG. 4F shows a temperature gradient of the skin at various depths during the heating stage by the dermal condition device of FIG. 3A for a pulse duration of 8 milliseconds, constructed and operative in accordance with another embodiment of the disclosed technique.

Reference is now made to FIG. 4F which shows a temperature gradient, generally referenced 478, of skin 250 at various depths during the heating stage by protrusion 338 (FIG. 3A) of dermal condition device 300 (FIG. 3A) for a pulse of 8 ms, constructed and operative in accordance with another embodiment of the disclosed technique. Although the effect on skin 250 is illustrated respective of dermal condition device 300 (FIG. 3A), this is not meant to be limiting and it is to be understood that a similar effect is produced on skin 250 by applying the heating stage by dermal conditioning device 200. Dashed line 482 indicates the border between stratum corneum layer 252 and deeper skin layers 254, 256 and 258. The indications of the skin depths are intended as exemplary only and are not to scale. The heat gradient of the region above dashed line 482 corresponds to curves 476A, 476B and 476C of FIG. 4E. The heat gradient of the region below dashed line 482 corresponds to curves 476D and 476E of FIG. 4E. Thus, the heating stage has a dual effect on skin 250. Stratum corneum layer 252 is heated to a relatively high temperature, as shown by curves 476A, 476B and 476C (FIG. 4F), affecting its elasticity. When stratum corneum layer 252 is at a relative humidity of 100% prior to the heating stage, its elongation in response to an applied stress is 200%. However, when stratum corneum layer 252 is at a relative humidity approaching 0% after the heating stage, its elongation in response to an applied stress decreases to less than 10%. By contrast, deeper skin layers 254, 256 and 258 are heated to a lower temperature, as shown by curves 476D and 476E (FIG. 4E).

Figure 5C:
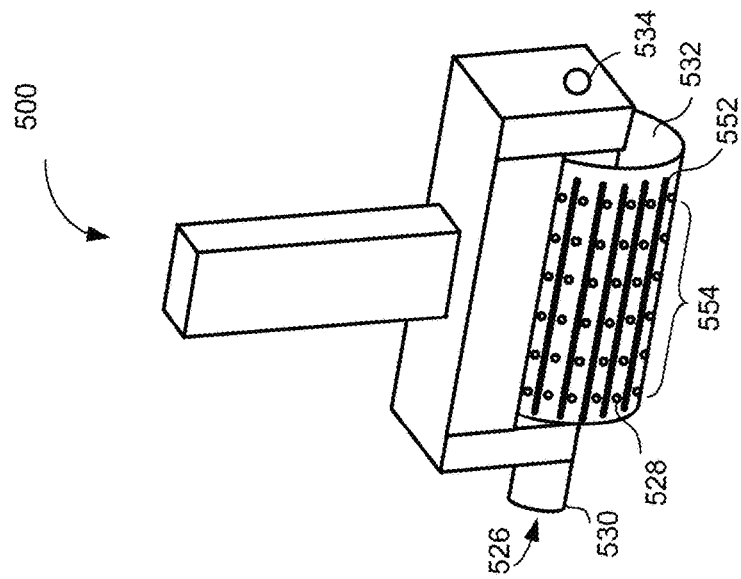
FIGS. 5A-5C are schematic illustrations of a dermal conditioning device of the disclosed technique that produces heat using an optical emitter, constructed and operative in accordance with another embodiment of the disclosed technique.
Figure 5B:
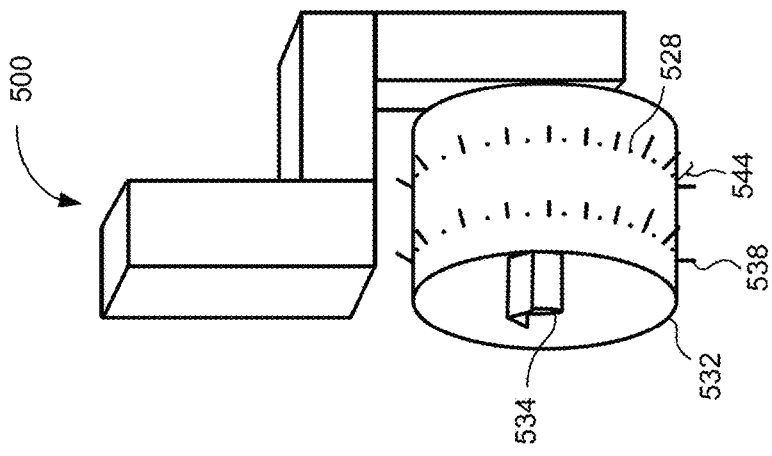
Figure 5A:
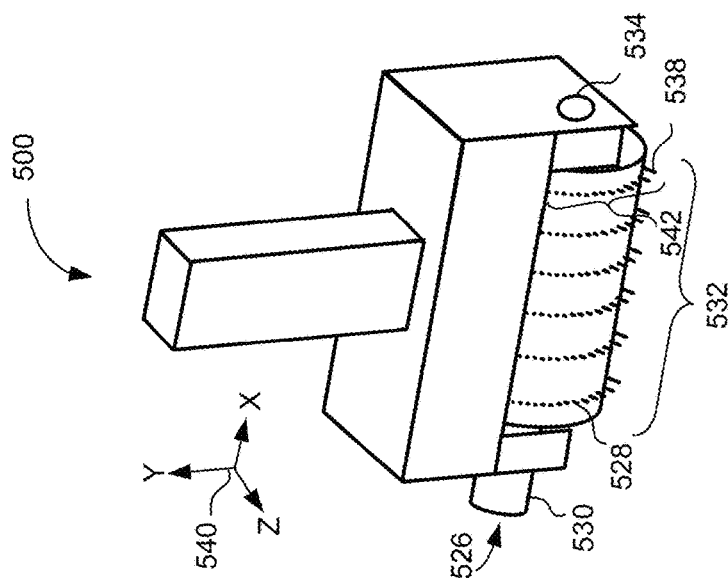

Reference is now made to FIGS. 5A-5C which are schematic illustrations of a dermal conditioning device of the disclosed technique that produces heat using an optical emitter, generally referenced 500, constructed and operative in accordance with another embodiment of the disclosed technique. Dermal conditioning device 500 produces heat using an optical emitter and generates stress by use of a rotatable cylinder that is operative to roll over the surface of the skin (not shown) and produce a strain on the skin. In the description that follows, dermal conditioning device 500 is understood to include at least the hardware components of dermal conditioning device 200 (FIGS. 2A-2E) and is operable to perform any of the procedures and functions described above with respect to skin 250. As mentioned above, dermal conditioning device 500 can function without the producing of heat and just via the stress generated by use of a rotatable cylinder and does not necessary produce tiny mechanical lesions in the eyelids. Dermal conditioning device 500 includes a controller (not shown) and a power supply (not shown), an actuator 530 and a roller 532 as well as a heat generator 526 and a heat emitter 528. The controller and the power supply correspond to controller 208 and power supply 210 (both from FIG. 2B). Heat generator 526 and heat emitter 528 correspond to heat generator 226 and heat emitter 228 (both from FIG. 2B). Actuator 530 and roller 532 correspond to actuator 230 and stress conveyor 232 (both from FIG. 2B). The controller, the power supply and heater 526 may be integrated within the body of dermal conditioning device 500.

Roller 532 is a rotatable cylinder that forms the distal end of dermal conditioning device 500 and is operative to directly contact and touch skin 250. Actuator 530 is electrically coupled to the power supply and the controller. Actuator 530 is mechanically coupled to roller 532 via a shaft 534. Shaft 534 is oriented orthogonally to the longitudinal y-axis of dermal conditioning device 500 and is positioned through a central axis of rotation parallel to the x-axis of dermal conditioning device of roller 532, thereby enabling roller 532 to rotate about shaft 534. An axis guide 540 of dermal conditioning device is shown in FIGS. 5A-5C. Actuator 530 can be embodied as a rotatable motor operative to rotate roller 532 about shaft 534.

Heat emitter 528 is formed of multiple channels that couple heat generator 526 to the distal end of dermal conditioning device 500 formed by roller 532. Heat generator 526 may be positioned in any suitable location within dermal conditioning device 500 such as inside roller 532. The channels of heat emitter 528 may be arranged in multiple rows forming parallel rings 542 covering the surface of roller 532. Roller 532 may be disposed with 1, 2, 3 . . . n parallel rings 542 of channels forming heat emitter 528. The distance between the rings may range from tens of micrometers to millimeters, such as 0.05 mm, 0.2 mm or 1 mm. The distance between any two of the channels may range from 0.1 mm to 0.5 mm, from 0.5 mm to 1 mm, from 1 mm to 1.5 mm, from 1.5 mm to 2 mm, from 2 mm to 2.5 mm or from 2.4 mm to 3 mm. All these distances are merely brought as examples.

With reference to FIGS. 5A-5B, dermal conditioning device 500 is shown with heat generator 526 configured as an optical emitter operative to emit light suitable for causing the evaporation of water from live tissue, as described above with respect to FIG. 3C. Heat generator 526 does not cause evaporation or coagulation of skin tissue itself. Heat generator 526 may be an IPL light source, an IR light source or a solid state laser diode and may emit a laser having a wavelength of approximately 2.94 µm. Heat emitter 528 is formed of multiple optical channels that are configured to convey the optical signal emitted by heat generator 526 to the external surface of roller 532 at the distal end of dermal conditioning device 500. The optical signal emitted by heat emitter 528 causes water to evaporate from skin 250. When heat generator 526 is an IPL light source or IR light source, one or more reflectors (not shown) may be mounted between heat generator 526 and heat emitter 528 to concentrate the emitted light to a narrower beam in a range of approximately twice the diameter of each channel of heat emitter 528. When heat generator 526 is a solid state laser, heat generator 526 includes multiple small diameter lasers (not shown), each mounted within one of the optical channels of heat emitter 528. Heat emitter 528 along with heat generator 526 and roller 532 can be considered an epidermal lesion generator.

With reference to FIG. 5A, heat emitter 528 is constructed as multiple optical channels embedded within multiple protrusions 538 covering roller 532. Heat generator 526 and heat emitter 528 of dermal conditioning device 500 are substantially similar to heat generator 326 (FIG. 3C) and heat emitter 328 (FIG. 3C) of dermal conditioning device 300 (FIG. 3C), with the notable difference that heat generator 526 and heat emitter 528 are disposed on the surface of roller 532. Protrusions 538 may be formed of any suitable biocompatible, thermally conductive and thermally resilient material, such as described above with respect to array of protrusions 338 (FIG. 3B). Similarly, the dimensions, shape and material of protrusions 538 and the distances there between may correspond to those of protrusions 338 of dermal conditioning device 300. Plurality of protrusions 538 depresses the surface of skin 250 in a non-invasive manner, in synchrony with the rotation of roller about shaft 534. Protrusions 338 are sufficiently dull so as to not penetrate skin 250 when treated by dermal conditioning device 500, and depress skin 250 to a depth ranging from 0.1 millimeters (mm) to 1 mm, or from 0.05 mm to 1.2 mm, or from 0.2 mm to 0.8 mm, or from 0.3 mm to 0.7 mm, or from 0.4 mm to 0.6 mm or any other suitable range such as 0.025 mm to 0.05 mm or from 0.05 mm to 0.7 mm. The depression of the surface of skin 250 by plurality of protrusions 538 however is sufficient to cause the activation of the corneal, menace and lacrimation reflexes when used on the eyelids. The sheer movement of plurality of protrusions 538 over the eyelids causes the activation of nociceptors in the eyelids which can trigger any of the corneal, menace and lacrimation reflexes via the indirect activation of nociceptors in the cornea and/or sclera. In another embodiment, protrusions 338 may be sufficiently sharp to penetrate skin 250 when treated by dermal conditioning device 500 and thus cause tiny mechanical lesions in the eyelid. In one embodiment, the diameter of each of array of protrusions 338 may range from being 0.05 mm, 0.1 mm, 0.15 mm and up to 1.0 mm. The height of protrusions 338, as measured from the outer perimeter of roller 532 may range from being 0.05 mm, 0.1 mm, 0.15 mm and up to 1.0 mm. Although protrusions 338 are shown as pins in FIGS. 5A-5B, they may have any suitable shape for applying stress to the skin, such as the pyramid shape described above with respect to FIGS. 3A-3C or as a plurality of vaporizing needles.

With reference to FIG. 5B, heat emitter 528 is configured as multiple optical channels embedded directly on surface roller 532, between protrusions 538. Thus, during treatment, there is a small distance, indicated via reference number 544, corresponding to the height of protrusions 538, between heat emitter 528 and the surface of the stratum corneum. The embodiments shown in FIGS. 5A-5B are intended for illustrative purposes. Thus, features such as the handle and housing for dermal conditioning device 500, are shown as conceptual illustrations only. Whereas the optical channels forming heat emitter 528 of dermal conditioning device 500 of FIG. 5A are embedded within plurality of protrusions 538, the optical channels forming heat emitter 528 of dermal conditioning device 500 of FIG. 5B are disposed on the surface of roller 532, in between plurality of protrusions 538. Thus, the areas of the skin directly affected by heat emitter 528 of FIG. 5A correspond to those areas of skin directly affected by plurality of protrusions 538. Furthermore, heat emitter 528 of dermal conditioning device 500 of FIG. 5A comes in direct contact with the skin. By contrast, the areas of the skin directly affected by heat emitter 528 of dermal conditioning device 500 of FIG. 5B are in between those areas of skin directly affected by plurality of protrusions 538. Furthermore, heat emitter 528 may not come in direct contact with the skin by a distance corresponding to the height of plurality of protrusions 538.

Reference is now made to FIG. 5C which shows a further embodiment for dermal conditioning device 500, constructed and operative in accordance with embodiment of the disclosed technique. In this implementation for dermal conditioning device 500, stress applier 552, corresponding to stress applier 232 (FIG. 2B) is formed as multiple elongated ridges spanning the width of roller 532. Heat emitter 528 is formed from multiple optical channels embedded directly on roller 532 and arranged into rows 554 spanning the width of roller 532. Rows 554 of heat emitter 528 are interleaved with the ridges of stress applier 552. The width of roller 532 may range from 0.5 cm to 4 cm. The rows 554 of channels forming heat emitter 528 are positioned in between the elongated ridges 552. The height of ridges 552 may range from 0.5 mm to 2 mm from the surface of roller 532. In one embodiment, the height of ridges 552 of FIG. 5C may be approximately 1.25 mm, similar to the dimensions of protrusions 538 of FIG. 3B. Similarly, ridges 552 of FIG. 5C may be made of a suitable thermally conductive and biocompatible material as protrusions 338 (FIG. 3B).

The rotation of roller 532 by actuator 530 determines the exposure time of area of skin 250 to light emitted by heat generator 526. Thus, the level of epidermis dehydration of the skin is a function of the rotational frequency of roller 532, as well as the power and wavelength of the optical signal emitted by heat generator 526. The controller (not shown) controls the rotational speed of roller 532 about shaft 534, as well as the pulse duration and intensity of the light emitted by heat generator 526 to dehydrate the skin while avoiding ablation, according to the disclosed technique. In the case of heat generator 526 being embodied as an IPL or solid state laser, the controller may synchronize the light pulse emitted by heater 526 with the rotational speed of actuator 538, to ensure that light is emitted only from the optical channels of heat emitter 528 while within a line-of-sight with area of skin 250. Controller 508 controls the velocity of roller 532 over the skin. For example the velocity may range from 1 mm/s to 5 mm/s. With respect to FIGS. 5A-5B, the combination of the spacing between the optical channels of heat emitter 528 on roller 532 together with the rotational frequency of roller 532, as controlled by the controller is calibrated such that at any given time, the temperature of the contact areas of skin 250 with any one of protrusions 538 is substantially affected by a single one of protrusions 538, such that there are regions in between the areas of the skin making contact with protrusions 538 that remain at normal human body temperature of 37° C. Similarly, with respect to FIG. 5C, the combination of the spacing between the optical channels of heat emitter 528 on roller 532 together with the rotational frequency of roller 532, as controlled by the controller is calibrated such that at any given time, the temperature of the contact areas of skin 250 with any one of ridges 552 is substantially affected by a single one of ridges 552, such that there are regions in between the areas of the skin making contact with ridges 552 that remain at normal human body temperature of 37° C.

After the skin has been dehydrated, such as may be determined by a timer, a sensor and the like, the controller controls the rotation of roller 532 to cause any of protrusions 538 (FIGS. 5A-5B), or alternatively ridges 552 (FIG. 5C) to apply a non-invasive compression load, or stress on the dehydrated skin, producing a strain on the skin that causes a plurality of fissures to form. The controller calibrates and controls the rotational speed of roller 532 and the subsequent pressure exerted by protrusions 538 (FIGS. 5A-5B), or alternatively by ridges 552 (FIG. 5C) on the skin so as to not puncture or penetrate the skin. As a result, the conditioning of skin 250 by dermal conditioning device 500 is non-invasive. It may be noted that the dehydration of the skin and the application of stress on the skin by dermal conditioning device 500 may be performed simultaneously, or sequentially, as controlled by the controller. By driving the rotation of roller 532 via actuator 530, and controlling the operation of heater 526, the controller controls the combined application of the heat and stress onto the skin producing the subsequent strain on the skin and causing the fissuring of the stratum corneum. As mentioned above, the disclosed technique may only include the application of stress on the skin by dermal conditioning device 500.

Figure 5D:
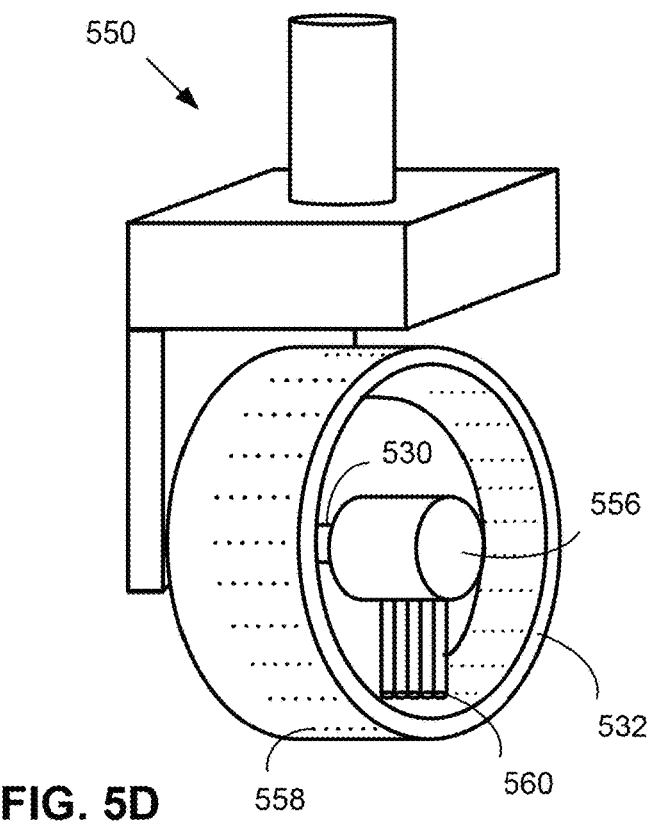
FIGS. 5D-5E are schematic illustrations of a dermal conditioning device of the disclosed technique that produces heat using a dry flow, constructed and operative in accordance with a further embodiment of the disclosed technique.
Figure 5E:
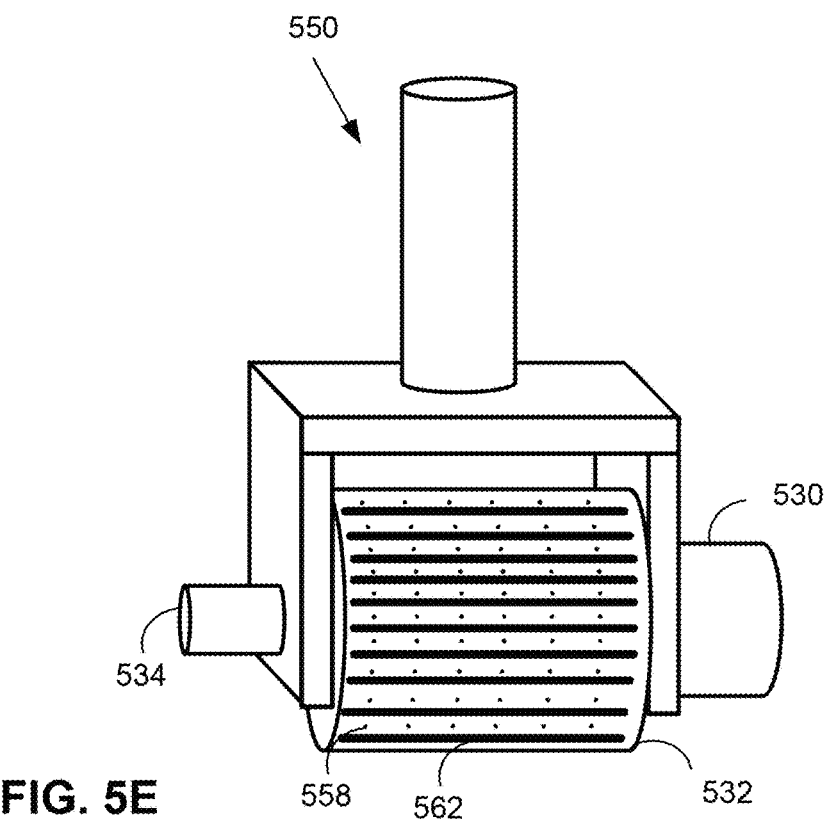

Reference is now made to FIGS. 5D-5E, which are schematic illustrations of a dermal conditioning device of the disclosed technique that produces heat using a dry flow, generally referenced 550, constructed and operative in accordance with a further embodiment of the disclosed technique. Dermal conditioning device 550 is understood to include at least the hardware components of dermal conditioning device 200 (FIGS. 2A-2E) and is operable to perform any of the procedures and functions described above with respect to skin 250. Dermal conditioning device 550 is substantially similar to dermal conditioning device 500 of FIGS. 5A-5C, having a roller 532 and an actuator 530 that operate as described above. Dermal conditioning device 550 includes a heat generator 556 and a heat emitter 558 coupled via a manifold 560. Manifold 560 along with heat generator 556 and heat emitter 558 together are operative to cause a flow of dry air or gas, referred to herein as a "dry flow", from heat generator 556 to be expelled from the distal end of dermal conditioning device 550 towards skin 250. The dry flow serves a dual purpose that both dehydrates the stratum corneum and deeper skin levels and additionally applies a stress as a steady fluid pressure, producing a strain on the skin that causes the stratum corneum to fissure. The combined dehydration and application of the stress by roller 532, heat generator 556 and heat emitter 558 may cause peeling of the stratum corneum, further contributing to the dehydration of the deeper skin layers, to condition the viable cells residing therein to subsequently absorb any of a hydrophilic, lipophilic or hydrophobic solution.

Heat emitter 558 is formed of multiple perforations on the surface of roller 532 that channel the dry flow produced by heat generator 556 via manifold 560 to the external surface of roller 532. Heat generator 556 generates the dry flow, for example by using an air dryer that heats air to a temperature ranging from 20° C. to 600° C. Manifold 560, illustrated as a plurality of tubes, channels the dry flow from heat generator 556 to roller 532, where the dry flow is expelled heat emitter 558, shown as perforations (not labeled) on the surface of roller 532. In some embodiments, the size of manifold 560 may range from being 0.5 mm and 0.6 mm up to 3 mm. The diameter of the perforations of heat emitter 558 on the outer surface of roller 532 may range from being 0.1 mm to 0.5 mm and up to 1 mm. The perforations of heat emitter 558 are aligned on the surface of roller 532 as multiple parallel rows or parallel rings. The distance between the perforations within a row may range from between 0.1 mm up to 3 mm. The distance between the rows may range from between 0.5 mm up to 3 mm.

In addition to the pressure exerted on the skin from the dry flow, roller 532 is operable to apply pressure on the surface of the skin. Thus the stress imposed on the skin is a combination of both the dry flow and the pressure from roller 532. The controller controls the timing, temperature and pressure of the dry flow and the rotational speed of roller 532 about shaft 534, thereby controlling the level of heat and stress delivered to the skin and the resulting strain produced on the skin. The level of heat is calibrated to cause sufficient dehydration of the skin to create fissures, without inducing trauma, as described in the heat calculations given above in equations 6-13.

With reference to FIG. 5E, another embodiment of dermal conditioning device 550 is shown, constructed and operative in accordance with an embodiment of the disclosed technique. In this embodiment for dermal conditioning device 550, roller 532 is additionally provided with one or more ridges 562 spanning the width of roller 532, such as described above with respect to FIG. 5C. The rows of channels forming heat emitter 558 are positioned in between the elongated ridges 562. In some embodiments, the velocity of roller 532 over the skin may range from 1 mm/s to 5 mm/s. The temperature of the dry flow emitted from dermal conditioning device 500 may range from 10° C. to 50° C. The humidity of the dry flow emitted from dermal conditioning device 550 may range from 0% to 10% humidity.

Each of the dermal conditioning devices shown in FIGS. 5A-5E can be used on the eyelids to cause a lesion in the epidermis and/or dermis of the eyelids thereby inducing the body's corneal, menace and lacrimation reflexes and additionally inducing the body's inflammatory healing process. The heat generator and heat emitter (which are both optional elements) in either of the dermal conditioning devices shown in FIGS. 5A-5E along with the shown rollers can constitute an epidermal and/or dermal lesion generator. The lesion or slight burn caused to the epidermis is sufficient to cause mild coagulation which activates the production of EGF. As described earlier, any perforations or penetration of the stratum corneum of the eyelids in this embodiment does not exceed 20-1000 μm and has a maximal width of approximately 700 μm. The depth of the perforations is controlled and regulated by a sensor, by a spacer or by other mechanisms (as described above in FIG. 3A) for ensuring that the depth of any tips, needles or vaporizing elements of the dermal conditioning device which enter the epidermis do not exceed 20-1000 μm. In addition, the amount of heat applied to the epidermis of the eyelids to cause an epidermal lesion or slight burn needs to be at least 37° C. in the embodiment where heat is used. The application of the dermal conditioning device of the disclosed technique to the eyelids is non-invasive yet causes minimal trauma to induce the body's corneal, menace and lacrimation reflexes as well as the body's natural inflammatory healing process. The aforementioned reflexes cause the contraction and relaxation of the orbicularis muscle thereby causing the eyes to blink and to exert physical pressure on the lacrimal and Meibomian glands in the eyelids which can treat DES and MGD. The body's natural inflammatory healing process includes the generation of EGF which can treat DES and MGD by increasing the production of meibum and sebum supply to the eye's tear film, thereby opening up any blocked acini and ducts in the eyelid from the Meibomian gland to the surface of the eye. The dermal conditioning device of the disclosed technique in this embodiment is to be used solely on the eyelids and should not come in contact with the surface of the eye (i.e., the sclera).

It is noted that regarding the mechanical lesions caused to the eyelids by the disclosed technique, the healing process of the skin may take up to about three months to fully recover. It can therefore be concluded that the treatment effect of the induced inflammatory healing process of the disclosed technique may last at least few weeks.

Reference is now made to FIGS. 6A-6B which are schematic illustrations of a dermal conditioning device of the disclosed technique that produces heat using an RF emitter, generally referenced 600A and 600B, respectively, constructed and operative in accordance with another embodiment of the disclosed technique. FIG. 6A illustrates an embodiment using a mono-polar electrode and FIG. 6B illustrates an embodiment using a set of bi-polar electrodes. In the description that follows, dermal conditioning device 600 is understood to include at least the hardware components of device 200 of FIGS. 2A-2E and is operable to perform any of the procedures and functions described above with respect to skin 250. In particular, dermal conditioning devices 600A and 66B each include a housing 620, a controller 608, a power supply 610, a linear motor 630, an RF generator 626 and either a single electrode 628A (FIG. 6A) or a pair of electrodes 628B (FIG. 6B) and a communications bus 616. Controller 608 corresponds to controller 208 (FIG. 2B), power supply 610 corresponds to power supply 210 (FIG. 2A), linear motor 630 corresponds to actuator 230 (FIG. 2B), RF generator 626 corresponds to heat generator (FIG. 2B), single electrode 628 of FIG. 6A corresponds to heat emitter 228 (FIG. 2B) and pair of electrodes 628B (FIG. 6B) corresponds to heat emitter 228 (FIG. 2B). Controller 608, power supply 610, motor 630 and RF generator 626 are integrated within housing 620 of respective dermal conditioning devices 600A and 600B. Electrode 628A of FIG. 6A is a mono-polar electrode whereas electrodes 628B of FIG. 6B are a set of bi-polar electrodes. Controller 608, power supply 610, motor 630 and RF generator 626 are electrically coupled via communications bus 616.

With reference to FIG. 6A, electrode 628A is electrically coupled to motor 630 and RF generator 626 of dermal conditioning device 600A. Electrode 628A is disposed at the distal end of dermal conditioning device 600A. Motor 630 is a linear motor that is operative to lightly push electrode 628A against skin 250, thereby applying a stress to dehydrated skin 250 to produce a strain causing the formation of fissures on the surface of skin 250. RF generator 626 produces a high frequency alternating electrical current that agitates the ions within stratum corneum layer 252 and deeper skin layers 254, 256 and 258, resulting in the heating of water stored therein via frictional heat, as indicated by dashed region 623A. In accordance with experimental results that have shown that water begins evaporating from tissue starting from a tissue temperature of 70° C. and approximately half of the tissue water content is lost when the tissue temperature reaches 104° C., controller 608 controls the heating of stratum corneum layer 252, and deeper skin layers 254, 256 and 258 via RF generator 626 to heat skin 250 to a temperature of up to 100° C. Controller 608 controls the pulse duration of the RF signal emitted by RF generator 604A to between 30-50 seconds. At this rate, the expected rise in temperature of skin 250 is substantially low. The maximal power delivered to skin 250 is approximately 25 W/m$^{2 \cdot °}$K with a frequency range of 460 KHz. When a single electrode is used, the heat penetrates a narrow, deep region, i.e. reaching into stratum spinosum layer 256. The combination of precisely controlled heating and application of stress causes the formation of fissures in stratum corneum layer 252 without substantially compromising or altering the previously existing immune and intact state of skin 250.

With reference to FIG. 6B, electrodes 628B are electrically coupled to motor 630 and RF generator 626 of dermal conditioning device 600B. Electrodes 628B are disposed at the distal end of dermal conditioning device 600B. Motor 630 is a linear motor that is operative to lightly push electrodes 628B against skin 250, thereby applying a stress to dehydrated skin 250, to produce a strain causing the formation of fissures on the surface of skin 250. The combination of precisely controlled heating and application of stress causes the formation of fissures in stratum corneum layer 252 without substantially compromising or altering the previously existing immune and intact state of skin 250. RF generator 626 produces a high frequency alternating electrical current that agitates the ions within stratum corneum layer 252 and deeper skin layers 254, 256 and 258, resulting in the heating of water stored therein via frictional heat, as indicated by dashed region 623B. Controller 608 controls the heating of stratum corneum layer 252 and deeper skin layers 254, 256 and 258 via RF generator 626 to heat skin 250 to a temperature of up to 100° C. Controller 608 controls the pulse duration of the RF signal emitted by RF generator 604A to between 30-50 seconds. At this rate, the expected rise in temperature of skin 250 is substantially low. The maximal power delivered to skin 250 is approximately 25 W/m$^{2 \cdot °}$K with a frequency range of 460 KHz. When two electrodes are used, the heat penetrates a wide shallow region as shown in FIG. 6B, i.e. the heat does not penetrate beyond stratum granulosum layer 254. The combination of precisely controlled heating and application of stress causes the formation of fissures in stratum corneum layer 252 without substantially compromising or altering the previously existing immune and intact state of skin 250.

Figure 6C:
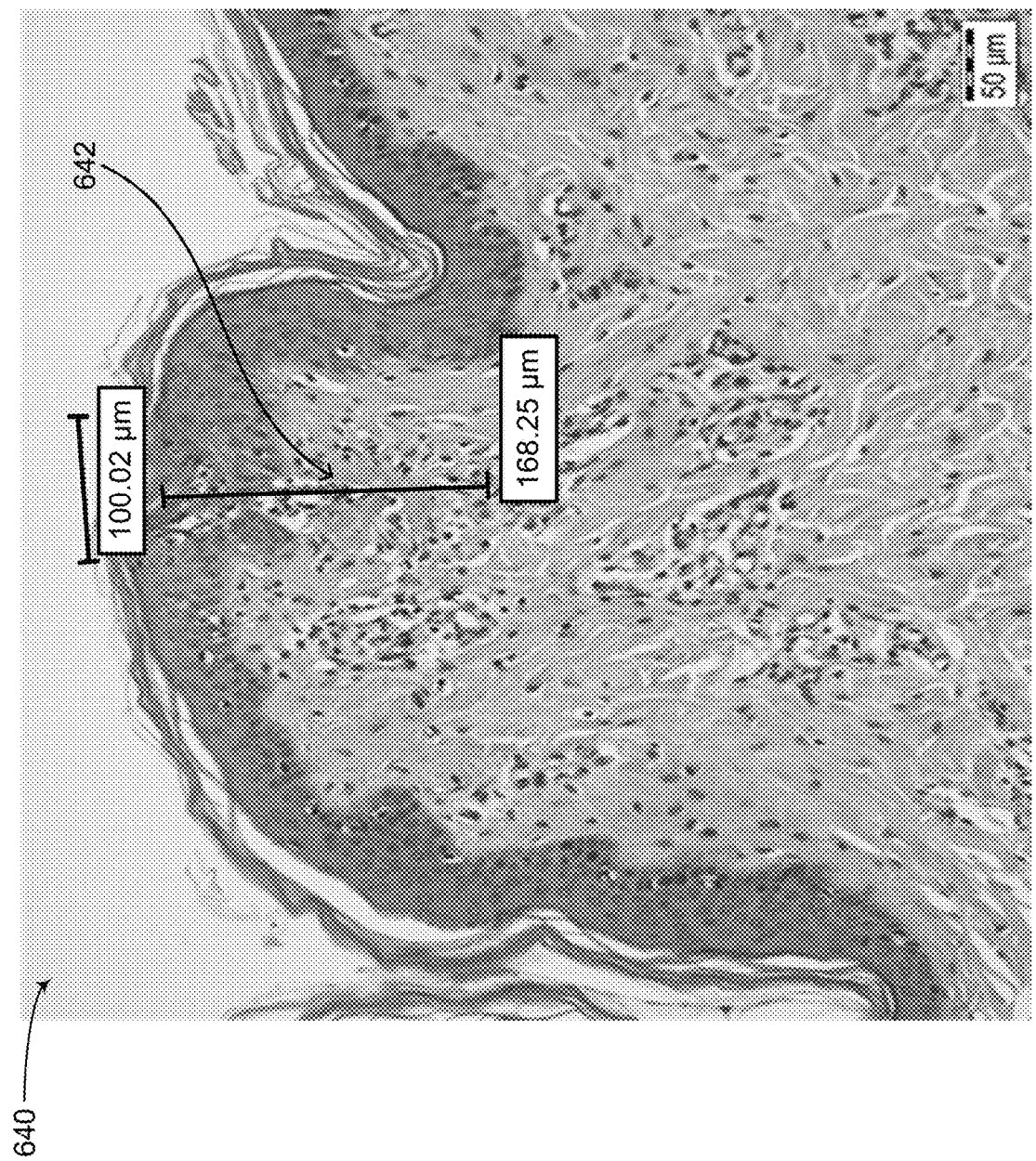
FIG. 6C is an image of an area of skin after undergoing the mechanical lesion treatment by the dermal conditioning device of FIGS. 6A-6B, constructed and operative in accordance with a further embodiment of the disclosed technique.

Reference is now made to FIG. 6C, which is an image of an area of skin after undergoing the mechanical lesion treatment by the dermal conditioning device of FIGS. 6A-6B, generally referenced 640, constructed and operative in accordance with a further embodiment of the disclosed technique. Similar to the area of skin shown above in FIG. 4A, shown in FIG. 6C is a lesion 642 having a width of 100.02 µm and a depth of 168.25 µm, thus extending into the upper region of the stratum spinosum layer and being sufficiently deep to cause an inflammatory response. FIG. 6C, like FIG. 4A, is merely brought as an example and shows a lesion generated by RF energy on pig skin.

It is noted that part of the disclosed technique relies on the body's process of nociception via nociceptors which are specialized peripheral sensory neurons that alert humans to potentially damaging stimuli at the skin by detecting extremes in temperature and pressure and injury-related chemicals. Nociceptors transduce these stimuli into long-ranging electrical signals that are relayed to higher brain centers. The activation of functionally distinct cutaneous nociceptor populations and the processing of information they convey provide a rich diversity of pain qualities. In the disclosed technique, the activation of corneal, menace and lacrimation reflexes is triggered by corneal and scleral nociceptors which are triggered by dermal nociceptors in the eyelids. In addition, the activation of the immune system's inflammatory response is triggering by the eyelid skin nociceptors. However from the perspective of a patient undergoing this treatment, there is low resultant pain due to the extremely short pulse durations used (2-60 ms) and the low energy used which prevents tissue coagulation (i.e., ablation of the epidermis of the eyelids).

Figure 7:
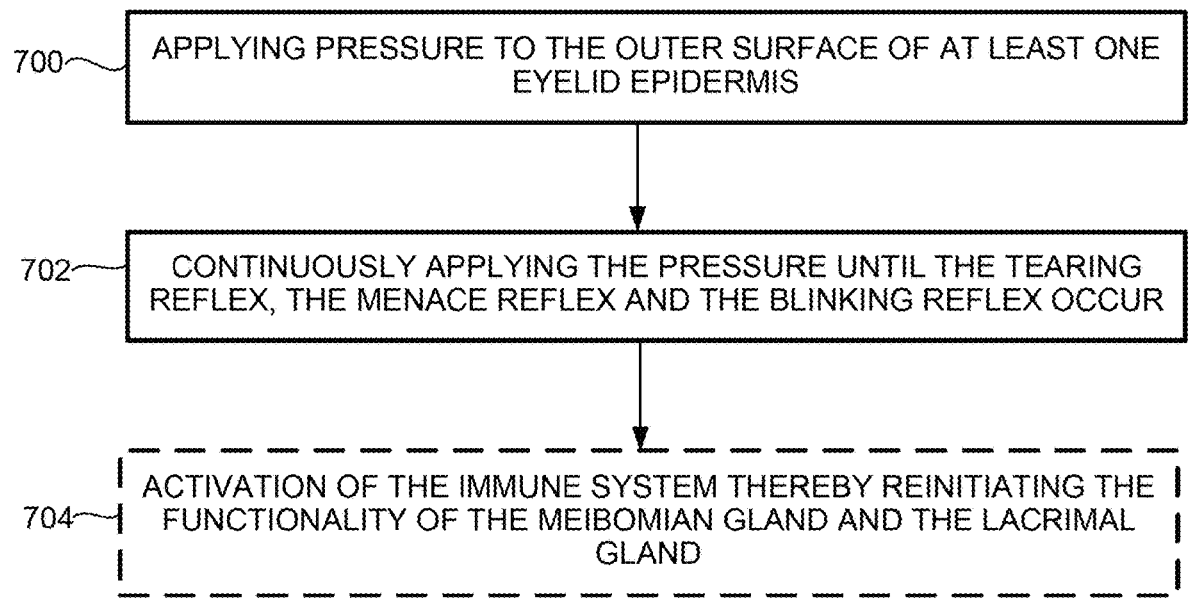
FIG. 7 is a schematic illustration of a method for operating a dermal conditioning device, constructed and operative in accordance with another embodiment of the disclosed technique.

Reference is now made to FIG. 7 which is a schematic illustration of a method for operating a dermal conditioning device, operative in accordance with another embodiment of the disclosed technique. In a procedure 700, pressure is applied to the outer surface of at least one eyelid epidermis. The pressure may be applied with a dull tip or surface thereby not forming a mechanical lesion on the eyelid epidermis or the pressure may be applied with at least one tip, protrusion and/or needle sufficiently sharp to form a mechanical lesion on the eyelid epidermis, as described above in FIG. 3B. The mechanical lesion may be generated such that is affects the epidermis or the epidermis and the dermis of the eyelid. The pressure may be applied using any of the devices described above in FIGS. 5A-5E and 6A-6B. The mechanical lesion may be generated by direct contact as described above in FIGS. 5A-5E and 6A-6B. The mechanical lesion according to the disclosed technique should have a maximal depth of 1000 µm and a maximal width of 700 µm, covering between 10-100% of the external surface of the eyelid. As mentioned above, the mechanical lesion generator (such as a heat or stressor with accompanying actuator tips, needles and/or protrusions) is positioned at least 3 mm from the eyelash line. Thus there is no direct contact between the device of the disclosed technique and either one of the Meibomian gland and/or lacrimal gland.

The device of the disclosed technique can be applied to the lower eyelid, upper eyelid or both.

With reference to FIG. 2A, controller 208 controls the generating of at least one signal by heater 204 and by stressor 206. Controller 208 controls any of the timing, intensity, a temperature, a frequency, a duration and a phase of the at least one signal. In one embodiment heater 204 and stressor 206 are separate components. In one embodiment heater 204 is not included in dermal conditioning device 200. With reference to FIG. 3A, controller 308 controls the generation of heat by heater 304 and controller 308 also controls the generation of stress by stressor 306. Heater 304 may maintain the distal end of dermal conditioning device 300 at 600 degrees Celsius. Stressor 306 may generate a pulse of a duration ranging between 8 milliseconds (ms) and 14 ms, or between 6 ms and 16 ms, or between 5 ms and 20 ms, or between 8 ms and 20 ms or between 2 ms to 60 ms. In another embodiment, heater 204 and stressor 206 are implemented as a single component. With reference to FIGS. 5D-5E, controller 508 controls the generation of a dry flow by heat generator 556.

In a procedure 702, the pressure is continuously applied until the tearing reflex (i.e., lacrimation reflex), the hand-blink reflex (i.e., menace reflex) and the blinking reflex (i.e., corneal reflex) occur. All tear production is apparently initiated by some external or internal stimuli. The continual application of pressure on the eyelid surface serves as an external stimuli for inducing the orbicularis muscle to contract and relax. This causes a tearing reflex as well as a blinking reflex which stimulates both the Meibomian gland and the lacrimal gland.

As mentioned above, reflex tearing is produced by strong physical and emotional stimulation of the lacrimal gland. The tears thus produced contain essential components, such as vitamin A and EGF, for the proliferation and differentiation of the corneal and conjunctival epithelium. As mentioned above, according to the disclosed technique, the generation of EGF leads to the following effect on the Meibomian glands. Based on evidence from in vitro cell culture, EGF may regulate Meibomian gland morphogenesis. Adding EGF to cultured, immortalized human Meibomian gland epithelial cells results in significant, time-dependent cell proliferation by upregulating genes of the cell cycle, DNA replication, ribosomes, translation and a significant decrease in those related to cell differentiation, tissue development, lipid metabolic processes and peroxisome proliferator-activated receptor signaling.

It is further noted that the effect of the treatment on the eyelid does not affect the viscosity of the Meibomian gland sebum or tear production by any mechanical or chemical means (i.e., not by temperature or by vibration). By activating the eye's lacrimation, menace and corneal reflexes to protect the cornea and tear film structure, an increase in upper tear layer lipids and proteins is generated by the Meibomian gland and the lacrimal gland. The activation of the eye's reflexes as mentioned above is sufficient to reinitiate the functionality of the Meibomian gland and the lacrimal gland, thereby providing relief from and treatment for DES and MGD.

The pressure applied in procedure 702 may also cause tiny mechanical lesions that further activate the eye's lacrimation, menace and corneal reflexes. The generation of tiny mechanical lesions may also cause the eyelid's inflammatory healing process to activate.

In a procedure 704, which is an optional procedure, the immune system (i.e., the inflammatory healing process) is activated to further reinitiate the functionality of the Meibomian gland and the lacrimal gland. The activation of the immune system by the generation of mechanical lesions on the eyelids activates the Meibomian gland and lacrimal gland in addition to causing the tearing reflex and the blinking reflex. The immune system can also be activated by the application of heat to the generation of mechanical lesions on the eyelid. Together, these further reinitiate the functionality of the Meibomian gland and lacrimal gland for a period of at least two weeks if not more.

As mentioned above, pressure can be applied and the mechanical lesion can be generated by generating a stress signal, where generating the stress signal includes performing any of: generating a dry flow, generating a radio frequency (herein abbreviated RF) signal, generating a series of mechanical pulses and generating a mechanical rotation. The stress is applied non-invasively to depress the external surface of the stratum corneum layer. In some embodiments the external surface of the stratum corneum layer is depressed to a depth ranging between 0.1 millimeters and 1 millimeter, or from 0.05 mm to 1.2 mm, or from 0.2 mm to 0.8 mm, or from 0.3 mm to 0.7 mm, or from 0.4 mm to 0.6 mm or from 0.025 mm to 0.05 mm or from 0.05 mm to 0.7 mm. The mechanical lesions can be further enhanced with the application of heat, from example from between 20° C.-600° C. With reference to FIGS. 5D-5E, heat generator 556 generates a dry flow that imposes a stress on stratum corneum layer 252. With reference to FIGS. 6A-6B, RF generator 626 generates a high frequency alternating electrical current that imposes a stress on stratum corneum layer 252. With reference to FIGS. 3A-3C, actuator 330 advances and retracts actuator tip 332 in a harmonic pulsating motion in accordance with a predefined pulse duration and a predefined number of pulses per treatment, as controlled by controller 308. Plurality of protrusions 338 depresses the surface of skin 250 in a non-invasive manner, in synchrony with the pulsating motion. The depression depth ranges between 0.1 millimeters (mm) to 1 mm, or from 0.05 mm to 1.2 mm, or from 0.2 mm to 0.8 mm, or from 0.3 mm to 0.7 mm, or from 0.4 mm to 0.6 mm or from 0.025 mm to 0.05 mm or from 0.05 mm to 0.7 mm. With reference to FIGS. 5D-5E, actuator 530 is mechanically coupled to roller 532 via shaft 534. Actuator 530 is a rotatable motor that causes roller 532 to rotate about shaft 534. Plurality of protrusions 538 depresses the surface of skin 250 in a non-invasive manner, in synchrony with the rotation of the roller about shaft 534.

In some embodiments of the disclosed technique, generating the at least one signal further includes controlling any of a timing, an intensity, a temperature, a frequency, a duration and a phase of the at least one signal. With reference to FIG. 2A, controller 208 controls any of the timing, intensity, a temperature, a frequency, a duration and a phase of a signal generated by any of heater 204 and stressor 206.

As described above, the disclosed technique can be used on the eyelids to treat DES and MGD. In addition, in some embodiments, the disclosed technique additionally allows the stratum corneum to be opened up for the application of a solution while keeping the barrier function of the skin intact. The application of strain (and optionally heat and optionally the generation of tiny mechanical lesions) on the eyelids, as described above, using the disclosed technique induces the body's corneal, menace and lacrimation reflexes while nevertheless not causing trauma or permanent damage to the eyelids. The optional application of heat as well as the generation of tiny mechanical lesions can also induce the body's inflammatory healing process while also not causing trauma or permanent damage to the eyelids. Causing the contraction and the relaxation of the orbicularis muscle and also inducing the body's inflammatory healing process leads to the increased production of EGF which can increase the flow of meibum and sebum, unblock acini and ducts in the Meibomian and lacrimal glands and thereby treat DES and MGD.

It will be appreciated by persons skilled in the art that the various embodiments disclosed herein above are intended as exemplary. The disclosed technique is not limited to the specific combinations and permutations of the elements described above. In particular, additional embodiments for a heater, a heat generator, a heat emitter, a stressor, an actuator and a stress applier, as are known in the art, may be combined in any suitable manner to achieve the disclosed technique.

It will be appreciated by persons skilled in the art that the disclosed technique is not limited to what has been particularly shown and described hereinabove. Rather the scope of the disclosed technique is defined only by the claims, which follow.

The invention claimed is:

1. A device for activating nociceptors on an eyelid of an eye for activating at least one of a corneal reflex, a menace reflex, and a lacrimation reflex of said eye, comprising:
   at least one skin tissue pressure generator comprising a plurality of heated tips, for generating at least one heated pressure signal;
   at least one controller coupled to said at least one skin tissue pressure generator, for controlling said at least one skin tissue pressure generator;
   a power supply coupled to said at least one skin tissue pressure generator and said at least one controller; and
   a housing encasing said at least one skin tissue pressure generator and said at least one controller;
   a distance gauge positioned at a distal end of said housing, for limiting a distance of a linear harmonic pulsating motion of said plurality of heated tips to a predetermined advancing depth into said eyelid;
   wherein said at least one controller controls said at least one skin tissue pressure generator to apply said at least one heated pressure signal to a predetermined advancing depth of said plurality of heated tips to stress an external surface of said eyelid;
   wherein said predetermined advancing depth is 400 micrometers or less;
   wherein said at least one skin tissue pressure generator applies said at least one heated pressure signal to said external surface of said eyelid such that there is intermittent direct contact between said plurality of heated tips and said external surface of said eyelid;
   wherein said at least one heated pressure signal is a generated pulse having a pulse duration on said external surface of said eyelid of 6 milliseconds or less;
   wherein said at least one heated pressure signal activates said nociceptors on said eyelid and nociceptors on said eye without tissue coagulation on said eye, thereby activating said at least one of said corneal reflex, said menace reflex and said lacrimation reflex of said eyelid.

2. The device according to claim 1, wherein said at least one skin tissue pressure generator further comprises at least one protrusion for generating at least one mechanical lesion on said external surface of said eyelid.

3. The device according to claim 1, further comprising a heat generator, for heating said plurality of heated tips, said plurality of heated tips being located at a distal end of said at least one skin tissue pressure generator.

4. The device according to claim 3, wherein said heat generator maintains said plurality of heated tips at a temperature ranging from 200 to 400 degrees Celsius.

5. The device according to claim 3, wherein said heat generator is selected from the group consisting of:
   i. a dry flow generator; and
   ii. a thermal heater.

6. The device according to claim 1, wherein said at least one controller controls said at least one heated pressure signal by controlling a first parameter of said at least one heated pressure signal, said first parameter selected from the group consisting of: a timing; an intensity; a frequency; a duration; a temperature and a phase, of said at least one heated pressure signal.

7. The device according to claim 1, wherein said at least one skin tissue pressure generator further comprises a stress applying generator selected from the group consisting of:
   i. a dry flow generator; and
   ii. a radio frequency generator.

8. The device according to claim 1, wherein said at least one skin tissue pressure generator comprises an actuator, electrically coupled with said at least one controller and mechanically coupled to a distal end of said at least one skin tissue pressure generator, said actuator configured to intermittently apply said at least one heated pressure signal to stress and heat said external surface of said eyelid.

9. The device according to claim 8, wherein said actuator is configured to:
   operate said at least one skin tissue pressure generator using said linear harmonic pulsating motion.

10. The device according to claim 8, wherein said plurality of heated tips are shaped as at least one protrusion configured to apply said at least one pressure signal to stress and heat said external surface of said eyelid.

11. The device according to claim 10, wherein said at least one protrusion has an optical channel embedded therein, said optical channel configured to apply said at least one heated pressure signal to stress and heat said external surface of said eyelid.

12. The device according to claim 10, further comprising a position sensor, coupled with said at least one skin tissue pressure generator, for determining an advancing depth of said at least one protrusion into said external surface of said eyelid.

13. The device according to claim 12, wherein said position sensor is selected from the group consisting of:
   i. an encoder;
   ii. a magnetic encoder;
   iii. an optical encoder; and
   iv. a Hall effect sensor.

14. The device according to claim 8, wherein said actuator is selected from the group consisting of:
   i. an electric motor;
   ii. a piezoelectric element;
   iii. an RF emitter;
   iv. a hydraulic piston;
   V. a pneumatic piston;
   vi. a magnetic piston;
   vii. a piezoelectric piston;
   viii. a solenoid actuator; and
   ix. a voice coil actuator.

15. The device according to claim 1, wherein said housing comprises a transparent material.

16. The device according to claim 1, wherein said distance gauge comprises a transparent material.

17. A method for activating nociceptors of an eyelid of an eye for activating at least one of a corneal reflex, a menace reflex, and a lacrimation reflex of said eye, comprising the procedures of:

generating at least one heated pressure signal on an external surface of said eyelid via a plurality of heated tips;

applying said at least one heated pressure signal to said external surface of said eyelid such that there is intermittent direct contact between said plurality of heated tips and said external surface of said eyelid via a linear harmonic pulsating motion of said plurality of heated tips; and controlling said applying of said at least one heated pressure signal by advancing said plurality of heated tips to a predetermined depth of said eyelid to stress and heat said external surface of said eyelid;

wherein said predetermined advancing depth is 400 micrometers or less;

wherein said at least one heated pressure signal is a generated pulse having a pulse duration on said external surface of said eyelid of 6 milliseconds or less;

wherein said at least one heated pressure signal activates said nociceptors on said eyelid and nociceptors on said eye without tissue coagulation on said eye, thereby activating said at least one of a corneal reflex, a menace reflex, and a lacrimation reflex of said eyelid.

18. The method according to claim 17, further comprising the procedure of generating at least one mechanical lesion with said at least one heated pressure signal, said at least one mechanical lesion having an advancing depth ranging between 5% to 90% depth of a thickness of said eyelid.

19. The method according to claim 18, wherein said procedure of generating said at least one mechanical lesion activates an immune system response of said eyelid thereby reinitiating functionality of at least one of a Meibomian gland and a lacrimal gland of said eye.

20. The method according to claim 17, wherein said at least one heated pressure signal is generated by performing an action selected from the group consisting of: generating a dry flow and generating a thermal heating signal, wherein said action is applied to said external surface of said eyelid without causing tissue coagulation of said eye.

21. The method according to claim 17, wherein said plurality of heated tips are maintained at a temperature ranging from 200 to 400 degrees Celsius.

22. The method according to claim 17, wherein said at least one heated pressure signal is generated by at least one stress signal, comprising performing an action selected from the group consisting of: generating a dry flow, generating a radio frequency signal and generating a series of mechanical pulses having a linear harmonic pulsating motion, wherein said action occurs without causing tissue coagulation of said eye.

23. The method according to claim 22, wherein generating said at least one stress signal comprises controlling a first parameter of said at least one stress signal, said first parameter selected from the group consisting of: a timing, an intensity; a frequency, a duration, a temperature and a phase, of said at least one stress signal.

24. The method according to claim 17, wherein said procedure of applying said at least one heated pressure signal comprises controlling a temperature of said plurality of heated tips.

* * * * *